United States Patent [19]

Bard et al.

[11] Patent Number: 5,714,089
[45] Date of Patent: Feb. 3, 1998

[54] LUMINESCENT METAL CHELATTE LABELS AND MEANS FOR DETECTION

[75] Inventors: Allen J. Bard, Austin, Tex.; George M. Whitesides, Newton, Mass.

[73] Assignee: IGEN International, Inc., Gaithersburg, Md.

[21] Appl. No.: 477,579

[22] Filed: Jun. 7, 1995

Related U.S. Application Data

[62] Division of Ser. No. 238,224, May 4, 1994, which is a continuation of Ser. No. 789,418, Nov. 4, 1991, Pat. No. 5,310,687, which is a continuation of Ser. No. 858,353, Apr. 30, 1986, abandoned, which is a continuation-in-part of Ser. No. 789,113, Oct. 24, 1985, Pat. No. 5,238,808, which is a continuation-in-part of Ser. No. 666,987, Oct. 31, 1984, abandoned.

[51] Int. Cl.$^6$ ............................ C09G 11/06; C07F 15/00
[52] U.S. Cl. ..................... 252/301.18; 252/301.16; 252/301.34; 252/301.35; 436/536; 436/800; 436/806; 546/2; 546/8
[58] Field of Search ............... 546/2, 8; 252/301.16, 252/301.18, 301.34, 301.35; 436/536, 800, 806

[56] References Cited

U.S. PATENT DOCUMENTS

| | | | |
|---|---|---|---|
| 3,504,052 | 3/1970 | Neuse et al. | 260/836 |
| 3,530,049 | 9/1970 | Scherzer et al. | 204/43 |
| 3,793,355 | 2/1974 | Wilkinson | 260/429 |
| 3,996,345 | 12/1976 | Ullman et al. | 424/12 |
| 4,058,732 | 11/1977 | Wieder | 250/461 |
| 4,199,559 | 4/1980 | Ullman et al. | 424/8 |
| 4,205,952 | 6/1980 | Cais | 23/230 |
| 4,220,722 | 9/1980 | Rowley | 435/188 |
| 4,238,195 | 12/1980 | Bogulaski et al. | 23/230 |
| 4,238,395 | 12/1980 | Buckler et al. | 260/326 |
| 4,277,437 | 7/1981 | Maggio | 422/61 |
| 4,280,815 | 7/1981 | Oberhardt et al. | 23/230 |
| 4,293,310 | 10/1981 | Weber | 23/230 |
| 4,352,751 | 10/1982 | Wieder et al. | 260/112 |
| 4,363,759 | 12/1982 | Bogulaski et al. | 260/112.7 |
| 4,374,120 | 2/1983 | Soini et al. | 436/546 |
| 4,378,344 | 3/1983 | Zahradnik et al. | 436/500 |
| 4,432,907 | 2/1984 | Wieder | 260/429.2 |
| 4,459,360 | 7/1984 | Marinkovich | 436/513 |
| 4,514,508 | 4/1985 | Hirschfeld | 436/518 |
| 4,637,988 | 1/1987 | Hinshaw et al. | 436/546 |
| 4,687,747 | 8/1987 | Lin | 436/518 |
| 4,699,978 | 10/1987 | Barton | 536/27 |
| 4,707,454 | 11/1987 | Hendrix | 436/546 |
| 4,721,669 | 1/1988 | Barton | 435/6 |
| 4,745,076 | 5/1988 | Muller et al. | 436/537 |
| 4,772,548 | 9/1988 | Stavrianpoulos | 435/5 |
| 4,943,523 | 7/1990 | Stavrianpoulos | 435/7 |
| 4,946,958 | 8/1990 | Campbell et al. | 546/104 |

FOREIGN PATENT DOCUMENTS

| | | |
|---|---|---|
| 0 178 450 | 4/1986 | European Pat. Off. |
| WO 81/01883 | 7/1981 | WIPO |

OTHER PUBLICATIONS

Blankespoor et al., Formation and Reactions of Dithiodicarbenium Salts—J. Am. Chem. Soc., vol. 103, No. 24, 1981, pp. 7097-7101.
Collings et al., Kinetics and Equilibria on the S–Netrosation of Alkylthioureas—J.S. Perkin II, pp. 1734-1736, 1975.
Curtis et al., Chemiluminescence: A New Method for Detecting Fluorescent Compounds Separated by Thin-Layer Chromatography, Journal of Chromatography, Journal of Chromatography, 134 (1977) 343-350.
Davidson, Chemical Abstracts, 108-146746(1988).
Doyle et al., Reversible Oxidation of 1,3–Dithiolan–2–thione–J.C.S. Chem. Comm., 1977, pp. 643-644.
Ege. D. et al., "Electrogenerated Chemiluminescent Determinatio of Ru(pby)$_3^{2+}$ at Low Levels", Anal. Chem. 56(13) 2413-17, 1984.
Gallagher et al., The Affinity of Carbon for Gold Complexes: Dissolution of Finely Disseminated Gold Using a Flow Electrochemical Cell—J. Electrochem. Soc., vol. 136, No. 9, Sept. 1989—2546-51.
Goldman, "Fluorescent Antibody Methods," Academic Press, New York (1968), pp. 97-117.
Hackh's Chemical Dictionary, 4th Edition, McGraw-Hill Book Company, New York, 1969, pp. 34-35.
Holzoecher et al., Anatlytical Application of Peroxyoxalte Chemiluminescence—Analytica Chimica Acta, 97 (1978) 21-27.
Ikariyama et al. "Electroluminescence—Based Homogeneous Immunoassay", Bioch. Bioph. Res. Com., 128(2), 987-992 (1985).

(List continued on next page.)

*Primary Examiner*—Joseph McKane
*Attorney, Agent, or Firm*—Curtis, Morris & Safford, P.C.; Barry Evans, Esq.; David Rubin, Esq.

[57] ABSTRACT

A chemical moiety is disclosed which comprises a chemical, biochemical, or biological substance attached to one or more electrochemiluminescent organometallic compounds. In a preferred embodiment of the invention the substance is attached to one or more ruthenium-containing or osmium-containing luminescent organometallic compounds. Methods are disclosed for detecting low concentrations of the chemical moiety using chemiluminescent, electrochemiluminescent, and photoluminescent means. Compounds are disclosed which are useful for labeling substances of interest with ruthenium-containing and osmium-containing labels or other electrochemiluminescent labels. These labeled substances are useful in methods provided for detecting and quantifying analytes of interest in binding assays and competitive binding assays. The labeled substances are of particular use in homogeneous binding assays. These methods form the bases for systems designed to enable the rapid, efficient, and sensitive determination of a broad array of chemical, biochemical, and biological materials of interest.

13 Claims, No Drawings

OTHER PUBLICATIONS

Johansen et., "Preparation and Properties of Surfactant Complexes of Ruthernium(II)." Aust. J. Chem. vol. 32 (1979) pp. 1453–1470.

Kalyanasundaram, J.C.S., Faraday Trans 2: 82(12):2401–15 (1986).

Keszthelyi, C., et al., "Electrogenerated Chemiluminesce: Determination of Absolute Luminescence Efficiency in Electrogenerated chemiluminescence: 9, 10-Diphenylanthracene-thianthrene and Other Systems:", Anal. Chem. 47(2), 249–5 (1975).

Maas et al., Dictation Disulfides by Reaction of thioreas and Related Compounds with Triflouromethanesulfonic Anhydride. The Role of Triflic Anhydride as an Oxidizing Agent—J. Org. Chem. 1981, 46, 1606–1610.

Sprintschnik, G., et al., "Preparation and Photochemical Reactivity of Surfactant Ruthenium (ii) Complexes in Monolayer Assemblies and at Water Solid Interfaces". J. Amer. Chem. Soc. 99(15) 4947–4 (1977).

Rubinstein et al., J. Amer. Chem. Soc., 103: 512–16 (1981).

Sedon et al., Flouroimmunoassay: Present Status and Key Problems—Clin. Chem. 25/3, 353–361 (1979).

Sonini et al., Flouroimmunoassay: Present Status and Key Problems—Clin. Chem. 25/3, 353–361 (1979).

Nichol, M.J., The Anodic Behaviour of Gold—Part I Oxidation in Acidic Solutions —Gold Bull, *13*,46–55, 1980.

White, H. et al. "Electrogenerated chemiluminescence and chemiluminescence of the Ru(2,2'-bpy)$_3^{2+}$ -S$_2$O$_8^{2-}$ System in Acetonitrile–Water Solutions," J. Amer. Chem. Soc. 104(25), 6891–5 (1982).

LUMINESCENT METAL CHELATTE LABELS AND MEANS FOR DETECTION

BACKGROUND OF THE INVENTION

This application is a division of application Ser. No. 08/238,224, filed May 4, 1994, pending, which is a continuation of prior application Ser. No. 07/789,418, filed Nov. 4, 1991, now U.S. Pat. No. 5,310,687, which in turn was a continuation of prior application Ser. No. 06/858,353, filed Apr. 30, 1986, now abandoned which is a continuation in part of application Ser. No. 06/789,113, filed Oct. 24, 1985, now U.S. Pat. No. 5,238,808, which is a continuation in part of application Ser. No. 06/666,987, filed Oct. 31, 1984, now abandoned.

There is a continuous and expanding need for rapid, highly specific methods of detecting and quantifying chemical, biochemical, and biological substances. Of particular value are methods for measuring small quantities of pharmaceuticals, metabolites, microorganisms and other materials of diagnostic value. Examples of such materials include narcotics and poisons, drugs administered for therapeutic purposes, hormones, pathogenic microorganisms and viruses, antibodies, metabolites, enzymes and nucleic acids.

The presence of these materials can often be determined by binding methods which exploit the high degree of specificity which characterizes many biochemcial and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which has been attached to one or more of the complexing materials.

The specific labeling method chosen often dictates the usefulness and versatility of a particular system for detecting a material of interest. A preferred label should be inexpensive, safe, and capable of being attached efficiently to a wide variety of chemical, biochemical, and biological materials without changing the important binding characteristics of those materials. The label should give a highly characteristic signal, and should be rarely, and preferably never, found in nature. The label should be stable and detectable in aqueous systems over periods of time ranging up to months. Detection of the label should be rapid, sensitive, and reproducible without the need for expensive, specialized facilities or personnel. Quantification of the label should be relatively independent of variables such as temperature and the composition of the mixture to be assayed. Most advantageous are labels which can be used in homogeneous systems, i.e., systems in which separation of the complexed and uncomplexed labeled material is not necessary. This is possible if the detectability of the label is modulated when the labeled material is incorporated into a specific complex.

A wide variety of labels have been developed, each with particular advantages and disadvantages. For example, radioactive labels are quite versatile, and can be detected at very low concentrations. However, they are expensive, hazardous, and their use requires sophisticated equipment and trained personnel. Furthermore, the sensitivity of radioactive labels is limited by the fact that the detectable event can, in its essential nature, occur only once per radioactive atom in the labeled material. Moreover, radioactive labels cannot be used in homogeneous methods.

Thus, there is wide interest in non-radioactive labels. These include molecules observable by spectrophotometric, spin resonance, and luminescence techniques, as well as enzymes which produce such molecules. Among the useful non-radioactive labeling materials are organometallic compounds. Because of the rarity of some metals in biological systems, methods which specifically assay the metal component of the organometallic compounds can be successfully exploited. For example, Cats, U.S. Pat. No. 4,205,952 (1980) discloses the use of immunochemically active materials labeled with certain organometallic compounds for use in quantitating specific antigens. Any general method of detecting the chosen metals can be used with these labels, including emission, absorption and fluorescence spectroscopy, atomic absorption, and neutron activation. These methods often suffer from lack of sensitivity, can seldom be adapted to a homogeneous system, and as with atomic absorption, sometimes entail destruction of the sample.

Of particular interest are labels which can be made to luminesce through photochemical, chemical, and electrochemical means. "photoluminescence" is the process whereby a material is induced to luminesce when it absorbs electromagnetic radiation. Fluorescence and phosphorescence are types of photoluminescence. "Chemiluminescent" processes entail the creation of the luminescent species by a chemical transfer of energy. "Electrochemiluminescence" entails the creation of the luminescent species electrochemically.

These luminescent systems are of increasing importance. For example, Mandle, U.S. Pat. No. 4,372,745 (1983) discloses the use of chemiluminescent labels in immunochemical applications. In the disclosed systems, the labels are excited into a luminescent state by chemical means such as by reaction of the label with $H_2O_2$ and an oxalate. In these systems, $H_2O_2$ oxidatively converts the oxalate into a high energy derivative, which then excites the label. This system will, in principle, work with any luminescent material that is stable in the oxidizing conditions of the assay and can be excited by the high energy oxalate derivative. Unfortunately, this very versatility is the source of a major limitation of the technique: typical biological fluids containing the analyte of interest also contain a large number of potentially luminescent substances that can cause high background levels of luminescence.

Another example of the immunochemical use of chemiluminescence which suffers from the same disadvantages is Oberhardt et al., U.S. Pat. No. 4,280,815, (1981) who disclose the in situ electrochemical generation of an oxidant (e.g., $H_2O_2$) in close proximity to an immunoreactant labeled with a chemiluminescent species. The electrogenerated oxidant diffuses to the chemiluminescent species and chemically oxidizes it, resulting in the net transfer of one or more electrons to the electrogenerated oxidant. Upon oxidation, the chemiluminescent species emits a photon. In contrast, the subject invention requires the direct transfer of electrons from a source of electrochemical energy to a chemiluminescent species which is capable of repeatedly emitting photons.

The present invention is concerned with electrochemiluminescent labels. Suitable labels comprise electrochemiluminescent compounds, including organic compounds and organometallic compounds. Electrochemiluminescent methods of determining the presence of labeled materials are preferred over other methods for many reasons. They are highly diagnostic of the presence of a particular label, sensitive, nonhazardous, inexpensive, and can be uesd in an wide variety of applications. Organic compounds which are suitable electrochemical labels include, for example, rubrene and 9,10-diphenyl anthracene. Many organometallic compounds are suitable electrochemical labels, but of particular use are Ru-containing and Os-containing compounds.

Thus, in one embodiment, the present invention is concerned with the use of Ru-containing and Os-containing labels which can be detected by a wide variety of methods. These labels are advantageous for many reasons that will be discussed herein.

Ru-containing and Os-containing organometallic compounds have been discussed in the literature. Cais discloses that any metal element or combination of metal elements, including noble metals from group VIII such as Ru, would be suitable components of organmetallic labels detectable by atomic absorption methods. (Cais, column 11, line 20). However, ruthenium is not a preferred metal in Cais, osmium is not specifically mentioned, no data are presented on the efficiency of using Ru or Os in any of the methods disclosed, and the preferred method of detection, atomic absorption, entails destruction of the sample.

Weber, U.S. Pat. No. 4,293,310 (1981), discloses the use of Ru-containing and Os-containing complexes as electrochemical labels for analytes in immunoassays. The disclosed complexes are linked to amino groups on the analytes through a thiourea linkage. Weber also suggests the possibility of forming carboxylate esters between the labels and hydroxy groups on other analytes.

According to Weber, the presence of the labeled materials can be determined with an apparatus and method which comprises a quencher and an electrochemical flow cell with light means. The photoelectrochemically active label upon photoexcitation transfers an electron to a quencher molecule; the oxidized molecule is subsequently reduced with an electron from an electrode of the flow cell which is held at suitable potential. This electron is measured as photocurrent. The amount of free labelled analyte in the system is determined by the photocurrent signal. Note that this method is the reverse of electrochemiluminescent detection of luminescent materials.

In subsequent reports, Weber et al. (1983), *Clinical Chemistry* 29, pp. 1665–1672, "Photoelectroanalytical Chemistry: Possible Interferences in Serum and Selective Detection of Tris(2,2'-bipyridine)ruthenium(II) in the Presence of Interferents," have discussed the problems associated with the use of this method to detect Ru-containing labels. In Table 2 of Weber et al., the extrapolated detection limit for tris(bipyridyl)ruthenium(II) is $1.1 \times 10^{-10}$ moles/L under optimal conditions. In anticipating that the actual use of these labels would entail measurements in the presence of complex mixtures, Weber et al. tested for potential interferents in their system. Table 3 of Weber et al. lists dimethylalkyl amines, EDTA, N-methylmorpholine, N,N'-dimethylpiperazine, hydroxide, oxalate, ascorbate, uric acid, and serum as interferents which would presumably the practical detection limit substantially above $1.1 \times 10^{-10}$ moles/L.

These studies were performed with a simple Ru-containing compound. No studies were reported in Weber or Weber et al. regarding the limits of detection of complex substances labelled with Ru-containing labels, or on whether the thiourea linkage between the labeled material and label is stable under conditions of the assay.

The particular labels with which the present invention is concerned are electrochemiluminescent. They can often be excited to a luminescent state without their oxidation or reduction by exposing the compounds to electromagnetic radiation or to a chemical energy source such as that created by typical oxalate-$H_2O_2$ systems. In addition, luminescence of these compounds can be induced by electrochemical methods which do entail their oxidation and reduction.

Extensive work has been reported on methods for detecting $Ru(2,2'\text{-bipyridine})_3^{2+}$ using photoluminescent, chemiluminescent, and electrochemiluminescent means: Rubinstein and Bard (1981), "Electrogenerated Chemiluminescence. 37. Aqueous Ecl Systems based on $Ru(2,2'\text{-bipyridine})_3^{2+}$ and Oxalate or Organic Acids", *J. Am. Chem. Soc.*, 103, pp. 512–516; and White and Bard (1982), "Electrogenerated Chemiluminescence. 41. Electrogenerated Chemiluminescence and Chemiluminescence of the $Ru(2,2'\text{-bpy})_3^{2+}$—$S_2O_8^{2-}$ System in Acetonitrile-Water Solutions", *J. Am. Chem. Soc.*, 104, p. 6891. This work demonstrates that bright orange chemiluminescence can be based on the aqueous reaction of chemically generated or electrogenerated $Ru(bpy)_3^{3+}$ (where "bpy" represents a bipyridyl ligand) with strong reductants produced as intermediates in the oxidation of oxalate ions or other organic acids. Luminescence also can be achieved in organic solvent-$H_2O$ solutions by the reaction of electrogenerated, or chemically generated, $Ru(bpy)_3^{1+}$ with strong oxidants generated during reduction of peroxydisulfate. A third mechanism for production of electrochemiluminescence from $Ru(bpy)_3^{2+}$ involves the oscillation of an electrode potential between a potential sufficiently negative to produce $Ru(bpy)_3^{1+}$ and sufficiently positive to produce $Ru(bpy)_3^{3+}$. These three methods are called, respectively, "oxidative-reduction," "reductive-oxidation," and "the $Ru(bpy)_3^{3+/+}$ regenerative system".

The oxidative-reduction method can be performed in water, and produces an intense, efficient, stable luminescence, which is relatively insensitive to the presence of oxygen or impurities. This luminescence from $Ru(bpy)_3^{2+}$ depends upon the presence of oxalate or other organic acids such as pyruvate, lactate, malonate, tartrate and citrate, and means of oxidatively producing $Ru(bpy)_3^{3+}$ species. This oxidation can be performed chemically by such strong oxidants as $PbO_2$ or a Ce(IV) salt. It can be performed electrochemically by a sufficiently positive potential applied either continuously or intermittently. Suitable electrodes for the electrochemical oxidation of $Ru(bpy)_3^{2+}$ are, for example, Pt, pyrolytic graphite, and glassy carbon. Although the oxalate or other organic acid is consumed during chemiluminescence, a strong, constant chemiluminescence for many hours can be achieved by the presence of an excess of the consumed material, or by a continuous supply of the consumed material to the reaction chamber.

The reductive-oxidation method can be performed in partially aqueous solutions containing an organic co-solvent such as, for example, acetonitrile. This luminescence depends upon the presence of peroxydisulfate and a means of reductively producing $Ru(bpy)_3^{1+}$ species. The reduction can be performed chemically by strong reductants such as, for example, magnesium or other metals. It can be performed electrochemically by a sufficiently negative potential applied either continuously or intermittently. A suitable electrode for the electrochemical reduction of Ru $(bpy)_3^{2+}$ is, for example, a polished glassy-carbon electrode. As with the oxidative-reduction method, continuous, intense luminescence can by achieved for many hours by inclusion of excess reagents, or by continous addition of the consumed reagents to the reaction mixture.

The $Ru(bpy)_3^{3+/+}$ regenerative system can be performed in organic solvents such as acetonitrile or in partially aqueous systems, by pulsing an electrode potential between a potential sufficiently negative to reduce $Ru(bpy)_3^{2+}$ and a potential sufficiently positive to oxidize Ru(bpy)$_3^{2+}$. A suitable electrode for such a regenerative system is, for example, a Pt electrode. This system does not consume chemical reagents and can proceed, in principle, for an unlimited duration.

These three methods of producing luminescent Ru-containing compounds have in common the repetitive oxidation-reduction or reduction-oxidation of the Ru-containing compound. The luminescence of solutions containing these compounds is therefore highly dependent on the electric potential of the applied energy source, and is therefore highly diagnostic of the presence of the Ru-containing compound.

Mandle cites Curtis et al. (1977), "Chemiluminescence; A New Method for Detecting Fluorescent Compounds Separated By Thin Layer Chromatography", *J. Chromatography* 134, pp. 343–350, as identifying Ru-tris(bipyridyl)(II) as a possible label in chemiluminescent applications. Curtis et al. reports only unpublished observations that Ru complexes can be induced to emit light when chemically excited by an oxalate/H$_2$O$_2$ system (Curtis et al. p. 350).

Neither Mandle nor Curtis recognized the exceptional utility of ruthenium and osmium complexes in chemiluminescent applications or the utility of electrochemiluminescent systems. Sprintschnik, G. et al. (1977), "Preparation and Photochemical Reactivity of Surfactant Ruthenium (II) Complexes in Monolayer Assemblies and at Water-Solid Interfaces", *J. Am. Chem. Soc.* 99, pp. 4947–4954, have described complexes of tris(2,2'-bipyridine)ruthenium(II) esterified with octadecanol or dehydrocholesterol, and have created monolayer films of these surfactant complexes. The complexes Were photoluminescent. But when the films were exposed to water, and then to light, the Ru-complexes failed to photoluminesce. This was attributed to photohydrolysis of ester groups in the presence of light.

It has been discovered, and is disclosed herein, that a wide variety of analytes of interest and chemical moieties that bind to analytes of interest may be conveniently attached to Ru-containing or Os-containing labels through amide or amine linkages. The labeled materials may then be determined by any of a wide variety of means, but by far the most efficient, reliable, and sensitive means are photoluminescent, chemiluminescent, and electrochemiluminescent means. It is also disclosed herein that electrochemiluminescent labels, including Ru-containing and Os-containing labels and organic molecules such as rubrene and 9,10-diphenyl anthracene, are particularly versatile and advantageous. The great advantages of the use of these novel labeled materials, and of the methods of detecting them, are further discussed hereinbelow.

SUMMARY OF THE INVENTION

According to the present invention, there is provided a chemical moiety having the formula

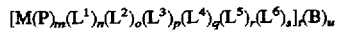

wherein M is ruthenium or osmium; P is a polydentate ligand of M; L$^1$, L$^2$, L$^3$, L$^4$, L$^5$ and L$^6$ are ligands of M, each of which may be a substance covalently bound to one or more of p, L$^1$, L$^2$, L$^3$, L$^4$, L$^5$ or L$^6$ through one or more amide or amine linkages; m is an integer equal to or greater than 1; each of n, o, p, q, r and s is zero or an integer; t is an integer equal to or greater than 1; u is an integer equal to or greater than 1; and p, L$^1$, L$^2$, L$^3$, L$^4$, L$^5$, L$^6$ and B are of such composition and number that the chemical moiety can be induced to emit electromagnetic radiation and the total number of bonds to M provided by the ligands of M equals the coordination number of M.

The present invention provides compounds particularly suitable as intermediates for attaching a luminescent ruthenium- or osmium-containing label to amino groups of chemical, biochemical and biological substance s. These intermediates are thus particularly suitable for creating chemical moieties according to the present invention. The intermediates are the mono- and di-N-hydroxysuccinimide esters of ruthenium or osmium bis(2,2'-bipyridine) (2,2'-bipyridine-4,4'-dicarboxylic acid) and their salts; and ruthenium or osmium bis(2,2'-bipyridine) (4,4'-di(chloromethyl)-2,2'-bipyridine). These compounds may be synthesized by means known in the art.

The present invention provides methods for determining the presence of the novel chemical moieties.

The present invention also provides methods of determining the presence of a chemcial moiety having the formula

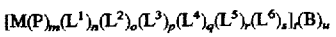

wherein M is ruthenium or osmium; P is a polydentate ligand of M; L$^1$, L$^2$, L$^3$, L$^4$, L$^5$ and L$^6$ are ligands of M, each of which may be a substance covalently bound to one or more of P, L$^1$, L$^2$, L$^3$, L$^4$, L$^5$, L$^6$ through one or more amide or amine linkages; m is an integer equal to or greater to or greater than 1; each of n, o, p, q, r and s is zero or an integer; t is an integer equal to or greater than 1; u is an integer equal to or greater than 1; and p, L$^1$, L$^2$, L$^3$, L$^4$, L$^5$, L$^6$ and B are of such composition and number that the chemical moiety can be induced to emit electromagnetic radiation and the total number of bonds to M provided by the ligands of M equals the coordination number of M.

The method comprises:

a) forming a reagent mixture under suitable conditions containing the chemical moiety;

b) inducing the moiety to emit electromagnetic radiation by exposing the reagent mixture to chemical energy or electrochemical energy; and c) detecting the emitted electromagnetic radiation and thereby determining the presence of the chemical moiety.

This invention further provides for the use of ruthenium-containing and osmium-containing labels in binding methods for determining the presence of substances of interest. These methods may be used to determine labeled moieties of interest, to employ labeled moieties to determine analytes of interest, or to use labelled analogues of analytes of interest to determine analytes of interest in competitive binding assays. These binding methods may be homogeneous or heterogeneous binding methods.

Still further, the present invention provides systems for determining the presence of the ruthenium-containing or osmium-containing chemical moieties of this invention. These systems comprise a means for inducing the chemical moiety to emit electromagnetic radition.

The present invention also provides systems for employing the ruthenium-containing or osmium-containing chemical moieties in binding methods for the determination of analytes of interest.

wherein A is a compound which can be induced to repeatedly emit electromagnetic radiation by direct exposure to an electrochemical energy source; B is a substance which is attached to A; k is an integer equal to or greater than 1, comprising a) forming a reagent mixture under suitable conditions containing the chemical moiety; b) inducing the chemical moiety to repeatedly emit electromagnetic radiation by directly exposing the moiety to electrochemical energy and c) detecting the emitted electromagnetic radiation and thereby determining the presence of the chemical moiety.

The present invention also provides for use of electrochemiluminescent labels in binding methods for determining the presence of substances of interest. These methods can be used to determine labeled moieties of interest, to employ labeled moieties to determine analytes of interest, or to use labeled analogues of analytes of interests to determine analytes of interest in competitive binding assays. These binding methods can be homogeneous or heterogeneous binding methods.

A specific embodiment of the invention provides for compositions which contain two or more different chemical moieties. Each of the moieties may be chemical species which can be induced to emit electromagnetic radiation of a different wavelength. In another embodiment of the invention the chemical moieties may be chemical species each of which is induced to emit electromagnetic radiation by exposure to energy of a different value or from a different source. A different substance or analyte of interest may then be specifically attached to each of the different chemical moieties. By using these compositions and methods it is possible to determine two or more different substances or analytes of interest that may be present in the sample under examinationl.

DETAILED DESCRIPTION OF THE INVENTION

According to the present invention, there is provided a chemical moiety having the formula

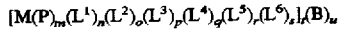

wherein M is ruthenium or osmium; P is a polydentate ligand of M; $L^1$, $L^2$, $L^3$, $L^4$, $L^5$ and $L^6$ are ligands of M, each of which may be the same as, or different from, each other ligand; B is a substance covalently bound to one or more of P, $L^1$, $L^2$, $L^3$, $L^4$, $L^5$ or $L^6$ through one or more amide or amine linkages; m is an integer equal to or greater than 1; each of n, o, p, q, r and s is zero or an integer.; t is an integer equal to or greater than 1; u is an integer equal to or greater than 1; and P, $L^1$, $L^2$, $L^3$, $L^4$, $L^5$, $L^6$ and B are of such composition and number that the chemical moiety can be induced to emit electromagnetic radiation and the total number of bonds to M provided by the ligands of M equals the coordination number of M.

In one embodiment of the invention M is ruthenium. In another embodiment of the invention M is osmium.

This chemical moiety must have at least one polydentate ligand of M. If the moiety has greater than one polydentate ligand, the polydentate ligands may be the same or different. Polydentate ligands include aromatic and aliphatic ligands. Suitable aromatic polydentate ligands include aromatic heterocyclic ligands. Preferred aromatic heterocyclic ligands are nitrogen-containing, such as, for example, bipyridyl, bipyrazyl, terpyridyl, phenanthrolyl and porphyrins.

Suitable polydentate ligands may be unsubstituted, or substituted by any of a large number of substituents known to the art. Suitable substituents include for example, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, maleimide sulfur-containing groups, phosphorus containing groups, and the carboxylate ester of N-hydroxysuccinimide.

Additionally, at least one of $L^1$, $L^2$, $L^3$, $L^4$, $L^5$ and $L^6$ may be a polydentate aromatic heterocyclic ligand. Furthermore, at least one of these polydentate aromatic heterocyclic ligands may contain nitrogen. Suitable polydentate ligands include, but are not limited to, bipyridyl, bipyrazyl, terpyridyl, phenanthroyl, a porphyrin, substituted bipyridyl, substituted bipyrazyl, substituted terpyridyl, substituted phenanthroyl or a substituted porphyrin. These substituted polydentate ligands may be substituted with an alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, maleimide a sulfer-containing group, a phosporus-containing group or the carboxylate ester of N-hydroxysuccinimide.

In one embodiment of the invention the chemical moiety contains two bidentate ligands, each of which is bipyridyl, bipyrazyl,, terpyridyl, phenanthrolyl, substituted bipyridyl, substituted bipyrazyl, substituted terpyridyl or substituted phenanthrolyl.

In another embodiment Of the invention the chemical moiety contains three bidentate ligands, each of which is bipyridyl, bipyrazyl, terpyridyl, phenanthrolyl, substituted bipyridyl, substituted bipyrazyl, substituted terpyridyl or substituted phyenanthrolyl. The chemical moiety may comprise ruthenium. In yet another embodiment of the invention, the chemical moiety comprises ruthenium, two bidentate bipyridyl ligands and one substituted bidentate bipyridyl ligand.

In still another embodiment of the invention the chemical moiety contains a tetradentate ligand such as a porphyrin or substituted porphyrin.

This chemical moiety may have one or more monodentate ligands, a wide variety of which are known to the art. Suitable monodentate ligands include, for example, carbon monoxide, cyanides, isocyanides, halides, and aliphatic, aromatic and heterocyclic phosphines, amines, stibines, and arsines.

Particularly preferred embodiments of this chemical moiety comprise bis (2,2'-bipyridyl)ruthenium(II) and tris(2,2'-bipyridyl)ruthenium(II).

It is within the scope of the invention for one or more of the ligands of M to be attached to additional chemical labels, such as, for example, radioactive isotopes, fluorescent components, or additional luminescent ruthenium- or osmium-containing centers.

It is also within the scope of this invention for the labeled substance (B) to be labeled by greater than one, e.g., two, three, four or more electrochemiluminescent centers.

Suitable substances (B) include many biological substances, for example, whole cells, viruses, subcellular particles, proteins, lipoproteins, glycoproteins, peptides, nucleic acids, polysaccharides, lipopolysaccharides, lipids, fatty acids, cellular metabolites, hormones, pharmacological agents, tranquilizers, barbiturates, alkaloids, steroids, vitamins, amino acids and sugars. Whole cell may be animal, plant, or bacterial, and may be viable or dead. Examples include plant pathogens such as fungi and nematodes. Within this application the term "subcellular particles" means subcellular organelles, membrane particles as from disrupted cells, fragments of cell walls, ribosomes, multi enzyme complexes, and other particles which can be derived from living organisms. Also, within this application, nucleic acids means chromosomal DNA, plasmid DNA, vital DNA, and recombinant DNA derived from multiple sources. Nucleic acids also include RNAs, for example messenger RNAs, ribosomal RNAs and transfer RNAs. Polypeptides include, for example, enzymes, transport proteins, receptor proteins, and structural proteins such as vital coat proteins. Preferred polypeptides are enzymes and serum-derived antibodies. Particularly preferred polypeptides are monoclonal antibodies. Hormones include, for example, insulin and T4 thyroid hormone. Pharmacological agents include, for example, cardiac glycosides. It is also within the scope of this invention to include synthetic substances which chemically resemble biological materials, such as synthetic peptides, synthetic nucleic acids, and synthetic membranes, vesicles and liposomes. The foregoing is not intended to be a comprehensive list of the biological substances suitable for use in this invention, but is meant only to illustrate the wide scope of the invention.

It is within the scope of this invention to include labeled nonbiological substances, including polymeric materials. These substances may be in the form of soluble polymeric molecules, or any of the large variety of known macroscopic forms such as, for example, beads, or containers such as test tubes, bottles, assay wells or the like.

Biological and nonbiological substances (B) are covalently bound to a ligand of M through one or more amide or amine linkages. In the case of amide linkages, the linkages may be oriented so that material (B) is bonded directly either to the carbonyl or to the nitrogen of the amide linkage. These chemical moieties may be ionized. If so, it is understood in the art that many different counterions will serve to neutralize the charge of preparations of the chemical moiety. Suitable cations include for example, $H^+$, $NH_4^+$, guanidinium, $Ag^+$, $Li^+$, $Na^+$, $K^+$, $Mg^{2+}$, $Mn^{2+}$, and $Cd^{2+}$. Suitable anions include, for example, halides, $OH^-$, carbonate, $SO_4^{2-}$, hexafluorophosphate and tetrafluoroborate.

The present invention also provides chemical moieties particularly suitable as intermediates for attaching a luminescent ruthenium-containing or osmium-containing label to amino groups of chemical, biochemical and biological substances. These intermediates are thus particularly suitable for synthesizing chemical moieties according to the present invention. The inventive intermediates are the mono- and di-N-hydroxysuccinimide esters of ruthenium and osmium 4,4'-(dicarboxy)-2,2'-bipyridyl, bis(2,2'-bipyridyl) and their salts; and ruthenium and osmium 4,4'-(dichloromethyl)-2, 2'-bipyridyl, bis(2,2' bipyridyl) and their salts.

The chemical structures of these intermediates are as follows: mono-N-hydroxysuccinimide esters of ruthenium or osmium 4,4'-(dicarboxy)-2,2'-bipyridyl, bis(2,2'-bipyridyl) having the formula

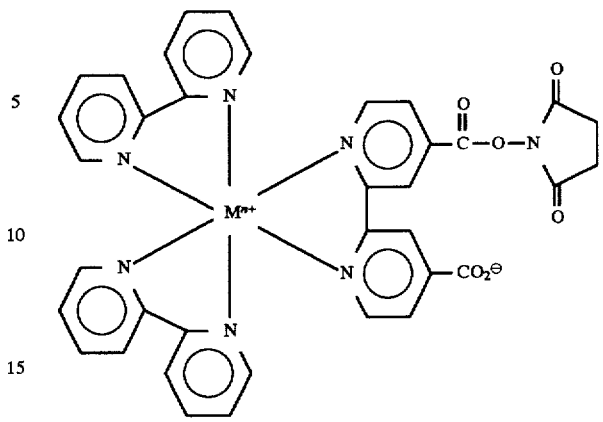

wherein M is Ru or Os, n is the integer 1, 2, or 3, and salts and stereoisomers thereof; di-N-hydroxysuccinimide esters of ruthenium- or osmium 4,4'-(dicarboxy)-2,2'-bipyridyl, bis(2,2'-bipyridyl) having the formula

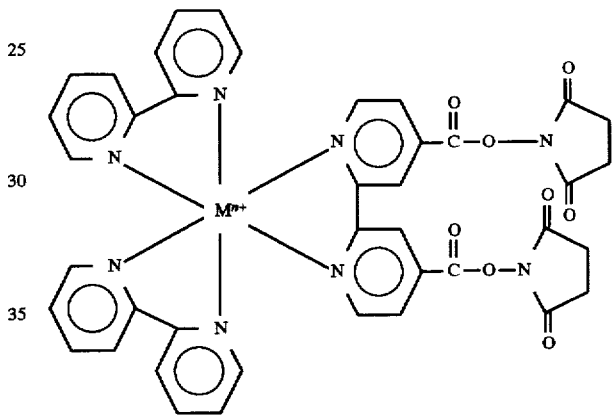

wherein M is Ru or Os, n is the integer 1, 2, or 3, and salts and stereoisomers thereof, and ruthenium or osmium 4,4'-(dichloromethyl)-2,2'-bipyridyl, bis(2,2'-bipyridyl) having the formula

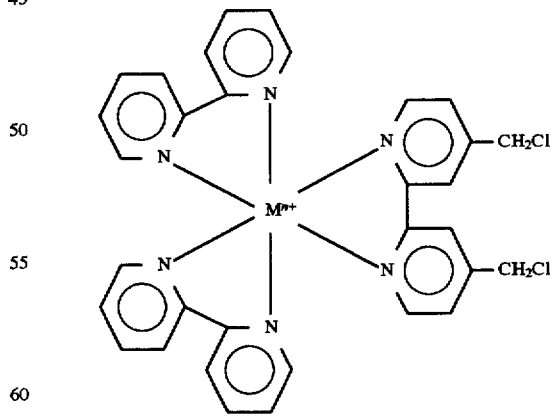

wherein M is Ru or Os, n is the integer 1, 2, or 3, and salts and stereoisomers thereof. These compounds may be synthesized by means known to the art.

A preferred method of synthesizing the ruthenium-containing N-hydroxysuccinimide esters is to first react ruthenium dichlorobis 2,2'-bipyridine) with 2,2'-bipyridine-4,4'-dicarboxylic acid in a hot aqueous methanol solution of sodium bicarbonate. After acidification, an aqueous solution of $NaPF_6$ is added to the solution of carboxylated ruthenium compound. The isolated hexafluorophosphate salt of the ruthenium complex is then esterified by reaction with N-hydroxysuccinimide in the presence of dicyclohexylcarbodiimide in dimethylformamide. Of course, many variations on the structure of the N-hydroxysuccinimide component are possible without substantially altering the usefulness of the inventive intermediates.

These intermediates may be ionized. If so, it is understood in the art that many different counterions will serve to neutralize the charge of preparations of the intermediate and form a salt. Suitable cations for forming these salts include for example $NH_4^+$, guandinium, $Ag^+$, $Li^+$, $Na^+$, $K^+$, $Ca^{2+}$, $Mg^{2+}$, $Mn^{2+}$, and $Cd^{2+}$. Suitable anions for forming these salts include, for example, halides, carbonate, $SO_4^{2-}$, hexafluorophosphate, and tetrafluoroborate.

These intermediates are useful for labeling substances containing a free amino group capable of attacking the carboxylate ester, and thereby displacing N-hydroxysuccinimide, or of attacking the chloromethyl group, and thereby displacing chloride. Use of these intermediates to label analytes of interest is preferred over the isothiocyanates of the prior art (e.g. Weber, U.S. Pat. No. 4,293,310). Isothiocyanates are generally prepared by reaction of a primary amine with carbon disulfide or thiophosgene, each of which is volatile and highly toxic. Carbon disulfide is also an acute fire and explosion hazard. The required precursor primary aromatic amines are more difficult to obtain than the precursor aromatic carboxylic acids used in the present invention. Also, the intermediates of the present invention are less reactive and more easily stored and handled than the isothiocyanate derivatives.

The present invention provides methods for determining the presence of the chemical moieties of the invention by forming a reagent mixture which comprises the chemical moiety and detecting the presence of the moiety in such reagent mixture. As such throughout this application, and as will be readily appreciated by those skilled in the art to which this invention pertains, "reagent mixture" includes any and all combinations of the chemical moieties with other substances or reagents which may be employed in the practice of this invention. The specific combination may be in the form of an aqueous or nonaqueous solution, a suspension or emulsion, a solid or semisolid, or a gas, limited only by such limitations as may be imposed by the detection method used to detect the presence of the chemical moiety.

The chemical moieties may be detected by methods well known in the art including, for example, emission and absorption spectroscopy, e.g. ultraviolet absorption, infrared absorption, and fluorescence emissions; atomic absorption, electrochemical, e.g. anodic stripping voltametry; neutron activation and chemical methods. Of particular interest are photoluminescence, chemiluminescence and electrochemiluminescence methods. In one embodiment of the invention, the presence of the chemical moiety may be determined by inducing the chemical moiety to emit electromagnetic radiation and detecting the emitted radiation. In another embodiment of the invention, the chemical moiety may be induced to emit electromagnetic radiation by exposing the reagent mixture to electromagnetic, chemical or electrochemical energy. In yet another embodiment of the invention, the chemical moiety may be induced to emit electromagnetic radiation by exposing the reagent mixture to chemical or electrochemical energy.

$Ru(bpy)_3^{2+}$ may be determined at very low concentrations using luminescence techniques. Using the oxidative reduction method, Ege et al. "Electrogenerated Chemiluminescent Determination of $Ru(Bpy)_3^{2+}$ At Low Levels", Analytical Chemistry 56:2413–2417 (1984), were able to detect $Ru(bpy)_3^{2+}$ at concentrations of $5 \times 10^{-8}$M. In these experiments, sodium oxalate was 1 mM in phosphate buffer pH 5.0, and the potential was pulsed at +1.0 to +1.4 volts versus a saturated sodium chloride reference electrode for 5 to 10 second intervals. These workers found the reductive oxidation method to be even more sensitive. Using 18 mM $Na_2S_2O_8$ and 0.1M tetra-n-butyl ammonium tetrafluoroborate in $CH_3CN:H_2O$ (1:1 v/v), $Ru(bpy)_3^{2+}$ concentrations as low as $10^{-13}$M could be detected. Further refinements of these techniques promise even greater sensitivity. These techniques also provide sensitive and accurate measurements of labeled substances, as demonstrated more fully in the examples set out hereinbelow.

Applicants' experience with $Ru(bpy)_3^{2+}$-labeled substances indicates the advantages of using ruthenium-containing and osmium-containing compounds as chemical labels. They are stable for long periods and may be attached efficiently to a wide variety of chemical, biochemical and biological materials. The labels are safe and relatively inexpensive. They give a highly characteristic signal and do not occur in nature. Measurements based on luminescence of the labels are sensitive, fast, reproducible and utilize-simple instrumentation. There is very little interference with detection based on luminescence of these labels by such components as phosphate buffered saline, Tween® (a surfactant), liver tissue extract or serum. Luminescence-based measurement of these labels does not destroy the sample or labeled materials and may be performed repetitively. The signal is generated repeatedly by each molecule of label, thereby enhancing the senstitivty with which these labels may be detected. The presence of labeled materials may be determined qualitatively or quantitatively depending on the needs of the particular application. The word "determined", as used in this patent application, refers to either qualitative or quantitative determinations of the labeled material.

Accordingly, this invention provides a method of determining the presence of a chemical moiety having the formula:

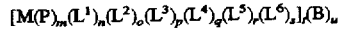

wherein M is ruthenium or osmium; P is a polydentate ligand of M; $L^1$, $L^2$, $L^3$, $L^4$, $L^5$ and $L^6$ are ligands of M, each of which may be the same as, or different from each other ligand; S is a substance which is a ligand of M or is attached to one or more of P, $L^1$, $L^2$, $L^3$, $L^4$, $L^5$ or $L^6$; m is an integer equal to or greater than 1; each of n, o, p, q, r and s is zero or an integer; t is an integer equal to or greater than 1; u is an integer equal to or greater than 1 and P, $L^1$, $L^2$, $L^3$, $L^4$, $L^5$ and $L^6$ and B are of such composition and number that the chemical moiety can be induced to emit electromagnetic radiation and the total number of bonds to M provided by the ligands of M equals the coordination number of M.

The method comprises:

a) forming a reagent mixture under suitable conditions containing the chemical moiety;

b) inducing the moiety to emit electromagnetic radiation by exposing the reagent mixture to chemical energy or electrochemical energy; and c) detecting the emitted electromagnetic radiation and thereby determining the presence of the chemical moiety.

Suitable conditions for forming the reagent mixture will be known to those skilled in the art and will depend on the type of reagent mixture involved. For example, suitable conditions for an aqueous reagent mixture may include appropriate concentrations of chemical moiety and other reagents such as oxidants, pH salt concentration and the like. For a solid sample, suitable conditions for forming a reagent mixture may include addition of a conducting liquid.

The methods of this invention include a method of determining the chemical moiety wherein the moiety is capable of binding to a chemical agent, i.e. forming a specific complex with the chemical agent.

Suitable chemical agents include, but are not limited to, whole cells, viruses, subcellular particles, nucleic acids, polysaccharides, proteins, glycoproteins., lipoproteins, lipopolysaccharides, lipids, fatty acids, peptides, cellular metabolites, hormones, pharmacological agents, tranquilizers, barbiturates, alkaloids, steroids, vitamins, amino acids, sugars or non-biological polymers.

In one embodiment of the invention, the chemical agent may be immobilized on the surface of an assay vessel. In another embodiment, the chemical agent may be a serum-derived antibody or a monoclonal antibody.

Of particular interest are antibody-antigen pairs of materials. This binding method may be used to determine the presence of labeled antigens, such as, for example, digoxin or digitoxin in complex mixtures such as blood, urine, or synthetic reaction mixtures by first exposing the mixture to immobilized antibodies specific for the antigen of interest, and then measuring the amount of labeled material bound to the immobilized antibodies.

The invention further provides methods for determining the presence of analytes of interest which bind to a chemical moiety, said moiety having the formula:

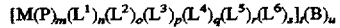

wherein M is ruthenium or osmium; P is a polydentate ligand of M; $L^1$, $n^2$, $L^3$, $L^4$, $L^5$ and $L^6$ are ligands of M, each of which may be the same as, or different from each other ligand; B is a substance which is a ligand of M or is attached to one or more of P, $L^1$, $L^2$, $L^3$, $L^4$, $L^5$ or $L^6$; m is an integer equal to or greater than 1; each of n, o, p, q, r and s is zero or an integer; t is an integer equal to or greater than 1; u is an integer equal to or greater than 1 and P, $L^1$, $L^2$, $L^3$, $L^4$, $L^5$, $L^6$ and B are of such composition and number that the chemical moiety can be induced to emit electromagnetic radiation and the total number of bonds to M provided by the ligands of M equals the coordination number of M.

The method comprises:

a) forming a reagent mixture under suitable conditions containing the chemical moiety;

b) inducing the moiety to emit electromagnetic radiation by exposing the reagent mixture to chemical energy or electrochemical energy; and c) detecting the emitted electromagnetic radiation and thereby determining the presence of the analyte of interest.

Also provided are methods of determining the presence of an analyte of interest wherein the analyte and a chemical moiety bind competitively to a complementary material, the chemical moiety having the formula:

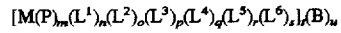

wherein M is ruthenium or osmium; P is a polydentate ligand of M; $L^1$, $L^2$, $L^3$, $L^4$, $L^5$ and $L^6$ are ligands of M, each of which may be the same as, or different from each other ligand; B is a substance which is a ligand of M or is attached to one or more of P, $L^1$, $L^2$, $L^3$, $L^4$, $L^5$ or $L^6$; m is an integer equal to or greater than 1; each of n, o, p, q, r and s is zero or an integer; t is an integer equal to or greater than 1; u is an integer equal to or greater than 1 and P, $L^1$, $L^2$, $L^3$, $L^4$, $L^5$, $L^6$ and B are of such composition and number that the chemical moiety can be induced to emit electromagnetic radiation and the total number of bonds to M provided by the ligands of M equals the coordination number of M.

The method comprises:

a) contacting the complementary material, the chemical moiety and the analyte under suitable conditions so as to form a reagent mixture;

b) inducing the chemical moiety to emit electromagnetic radiation by exposing the reagent mixture to electrochemical or chemical energy; and c) detecting the emitted electromagnetic radiation and thereby determining the analyte of interest.

Within this application "complementary material" means any substance capable of forming complexes with both an analyte of interest and a labeled analyte of interest or a labeled analogue of an analyte of interest.

The phrase "inducing to emit electromagnetic radiation" refers to creating an excited statee of said moiety which luminesces at wavelengths between 200 nanometes and 900 nanometers at ambient temperatures. The present invention envisions osmium-containing moieties as well as ruthenium-containing moieties and encompasses the wide variety of luminescent moieties which can be made by varying the chemical structure of the ligands. Each of these variations in the metal and the ligands can change the precise value of the energy input required to create the luminescent excited state. Similarly, the wavelength of the emitted electromagnetic radiation will be dependent upon the nature and environment of the ruthenium-containing or osmium-containing material. Generally, photoluminescence excitation and emission will occur with electromagnetic radiation of between about 200 nanometers and about 900 nanometers in wavelength. Chemiluminescent and electrochemiluminescent emission will generally occur with the emitted electromagnetic radiation being between about 200 nanometers and about 900 nanometers in wavelength. The potential at which the reduction or oxidation of the chemical moiety will occur depends upon its exact chemical structure as well as factors such as the pH of the solution and the nature of the electrode used. Generally, it is well known in the art how to determine the optimal emission and excitation wavelengths in a photoluminescent system, and the optimal potential and emission wavelength of an electrochemiluminescent and chemiluminescent system.

It should be clear that there are many methods for quantifying the amount of luminescent species present. The rate of enery input into the system can provide a measure of the luminescent species. Suitable measurements include, for example, measurements of electric current when the luminescent species is generated electrochemically, the rate of reductant or oxidant utilization when the luminescent species is generated chemically or the absorption of electromagnetic energy in photoluminescent techniques. In addition, of course, the luminescent species can be detected by measuring the emitted electromagnetic radiation. All of these measurements can be made either as continuous, rate-based measurements, or as cumulative methods which accumulate the signal over a long period of time. An example of rate-based measurements is the use of photomultiplier tubes, photodiodes or phototransistors to produce electric currents proportional in magnitude to the incident light intensity. Examples of cumulative methods are the integration of rate-based data, and the use of photographic film to provide cumulative data directly.

All of these luminescence-based methods entail repeated luminescence by the ruthenium-containing compound. The repetitive nature of the detectable event distinguishes these labels from radioactive isotopes or bound chemiluminescent molecules such a luminol. The latter labels produce a detectable event only once per molecule (or atom) of label, thereby limiting their detectability.

In the chemical moieties useful in these methods, biological and nonbiological substances (B) may be incorporated into the moieties by coordination directly to M or by attachment to a ligand of M. Attachment may be through covalent bonding, or by electrostatic or hydrogen bonding. Many diverse means of effecting covalent bonding of substances (B) to ligands of M are available. The attaching linkage may be, for example, an amide or amine bond, an ester or thioester, an ether or thioether, or any of many other means known to the art. The type of linkage will be determined by the substituents of the ligand and the suitable chemical groups available for binding with the ligand on the substance that is to be labeled.

The analyte of interest and the chemical moiety may be any pair of substances which are capable of binding together in a specific manner. Such substances include for example, whole cells, viruses, subcellular particles, nucleic acids, polysaccarides, proteins, glycoproteins, lipoproteins, lipopolysaccarides, lipids, fatty acids, peptides, cellular metabolites, hormones, pharmacological agents, tranquilizers, barbiturates, alkaloids, steroids, vitamins, amino acids, sugars, and non-biological polymers. Of particular interest are antibody-antigen pairs. One embodiment of the invention provides the use of labeled antibodies to determine the presence of cell surface antigens, or to label particular cells for detection by cell sorting methods. Antigens immobilized by, for example, attachment to immobilized, unlabeled antibodies can be detected by labeled antibodies in a method commonly known as a "sandwich" method.

In one embodiment of the invention, B is a nucleotide or a polynucleotide. In another embodiment, B is a serum-derived antibody or a monoclonal antibody.

In competitive binding assays, B may be the same substance as the analyte of interest or an analogue of the analyte, and capable of participating in the formation of a specific complex with a complementary material. Such analytes and complementary materials include, whole cells, viruses, subcellular particles, nucleic acids, polysaccharides, proteins, glycoproteins, lipoproteins, lipopolysaccharides, lipids, fatty acids, peptides, cellular metabolites, hormones, pharmacological agents, tranquilizers, barbiturates, alkaloids, steroids, vitamins, amino acids, sugars and non-biological polymers. Examples of such analytes and complementary materials include insulin, digoxin, digitoxin, T4 thyroid hormone, a fungus or nematode, a serum-derived antibody or a monoclonal antibody, a DNA fragment or an RNA fragment. Of particular interest are antibody-antigen-based methods. These methods are analogous to the well known radioimmunoassay, wherein an analyte of interest is detected when it displaces a radioactive analogue of the analyte from an antibody. The many variations on radioimmunoassay known to the art can, in principle, be used to advantage by employing moieties labeled according to the present invention in place of radioactively labeled compounds.

The present invention further provides heterogeneous and homogeneous binding methods which utilize the chemical moieties provided herein. In heterogeneous binding methods, the bound labeled substance must be physically separated from the unbound labeled substance before measurement of the presence of label. This is frequently accomplished in antibody-antigen systems by immobilizing one component, the antibody for example, by attachment to an insoluble matrix such as a filter or to the surface of beads or reaction vessels such as test tubes. The antigen-containing solution is poured through the filter or into the reaction vessel, and then washed away from the filter or sides of the reaction vessel. Only antigen specifically bound to antibody will remain to be determined.

In homogeneous methods, by contrast, the bound and unbound labeled material are present in the same reaction mixture when the presence of label is measured. This is possible when binding modifies the properties of the signal detectable from the label. There are many ways that luminescent labels can be used in homogeneous systems. For example, binding of the analyte to the chemical moiety can directly influence the signal detectable from the label. Additionally, a luminescence quencher may be positioned on an antibody so that binding of a labeled antigen to the antibody could result in suppression of the luminescence of the label by the luminescence quencher on the antibody. Many homogeneous methods for luminescent labels are known to the art, and some of them are reviewed in Boguslaski and Li (1982), "Homogeneous Immunoassays," *Applied Biochemistry and Biotechnology*, 7, pp. 401–414.

In one embodiment of the invention, the analyte is fixed to an insoluble matrix. Such a method may be performed as a sandwich assay i.e. the chemical moiety becomes bound to the immobilized analyte and unbound moiety is washed away from the matrix.

Another embodiment comprises a chemical agent to which the moiety is capable of binding being fixed to an insoluble matrix and the chemical moiety being a component of a biological fluid or synthetic reaction.

Additionally, the competitive binding methods of the present invention may comprise the complementary material being fixed to an insoluable matrix.

Both the heterogeneous and homogeneous competitive methods of the present invention comprise the complementary material being a monoclonal antibody and the insoluble matrix being the surface of an assay vessel.

The methods of the present invention may be performed by exposing the reagent mixture to electrochemical energy or to chemical energy. Additionally, the reagent mixture may be exposed to a combination of electromagnetic radiation, chemical energy, and electrochemical energy.

The chemical moiety may be oxidized by exposure to an energy source. Such an energy source may be a chemical oxidizing agent. Examples of such oxidizing agents include Ce(IV) salts or $PbO_2$. Furthermore, the chemical moiety may be reduced by exposure to an energy source. Such an energy source may be a chemical reducing agent. An example of a suitable reducing agent is magnesium.

The methods of the present invention may comprise inducing the chemical moieties to emit electromagnetic radiation more than once.

The reagent mixture may comprise oxalate, pyruvate, lactate, malonate, citrate, tartrate or peroxydisulfate. Furthermore, the chemical moiety may be reduced by exposure to an energy source and the reagent mixture may comprise peroxydisulfate. Moreover, the chemical moiety may be oxidized by exposure to an energy source and the reagent mixture may comprise oxalate, pyruvate, lactate, malonate, citrate or tartrate.

Methods of detecting the chemical moiety are provided wherein the reagent mixture is continously exposed to an electrode whose potential oscillates between a potential sufficient to effect the reduction of said chemical moiety and a potential sufficient to effect the oxidation of the chemical moiety.

The chemical moiety may be oxidized by exposure to an electrode whose potential oscillates above and below a potential sufficient to oxidize the chemical moiety, the reagent mixture comprising oxalate, pyruvate, lactate, malonate, tartrate or citrate. Moreover, the chemical moiety may be oxidized by exposure to an electrode whose potential is constant and sufficient to oxidize it, the reagent mixture comprising oxalate, pyruvate, lactate, malonate, tartrate or citrate.

The chemical moiety may also be reduced by exposure to an electrode whose potential oscillates above and below a potential sufficient to reduce it, the reagent mixture comprising peroxydisulfate. Such reagent mixture may additionally comprise acetonitrile. Furthermore, the chemical moiety may be reduced by exposure to an electrode whose potential is constant and sufficient to reduce it, the reagent mixture comprising peroxydisulfate. Such reagent mixture may also comprise acetonitrile.

When the chemical moiety is exposed to electrochemical or chemical energy, the emitted electromagnetic radiation may be continuously detected. Such electromagnetic radiation may be detected visually or with a photodiode. Furthermore, when the chemical moiety is exposed to electrochemical or chemical energy, the emitted radiation may be detected cumulatively, e.g. with a photographic film.

The present invention also provides a system for determining the presence of a chemical moiety having the formula:

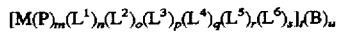

wherein M is ruthenium or osmium; P is a polydentate ligand of M; $L^1, L^2, L^3, L^4, L^5$, and $L^6$ are ligands of M, each of which may be the same as, or different from, each other ligand; B is a substance covalently bound to one or more of P, $L^1, L^2, L^3, L^4, L^5$ or $L^6$ through one or more amide or amine linkages; m is an integer equal to or greter than 1; each of n, o, p, q, r and s is zero or an integer; t is an integer equal to or greater than 1; u is an integer equal to or greater than 1; and P, $L^1, L^2, L^3, L^4, L^5, L^6$ and B are of such composition and number that the chemical moiety can be induced to emit electromagnetic radiation and the total number of bonds to M provided by the ligands of M equals the coordination number of M.

The system comprises:
a) a reagent mixture comprising the chemical moiety;
b) means for inducing the chemical moiety to emit electromagnetic radiation; and
c) means for detecting the emitted·electromagnetic radiation.

A system for determining the presence of an analyte of interest which binds to a chemical moiety is also provided, the moiety having the structural formula:

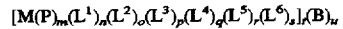

wherein M is ruthenium or osmium; P is a polydentate ligand of M; $L^1, L^2, L^3, L^4, L^5$, and $L^6$ are ligands of M, each of which may be the same as, or different from, each other ligand; B is a substance covalently bound to one or more of P, $L^1, L^2, L^3, L^4, L^5$, or $L^6$ through one or more amide or amine linkages; m is an integer equal to or greater than 1; each of n, o, p, q, r and s is zero or an integer; t is an integer equal to or greater than 1; u is an integer equal to or greater than 1; and P, $L^1, L^2, L^3, L^4, L^5, L^6$ and B are of such composition and number that the chemical moiety can be induced to emit electromagnetic radiation and the total number of bonds to M provided by the ligands of M equals the coordination number of M.

The system comprises:
a) the chemical moiety;
b) a means for contacting the chemical moiety with the analyte of interest to form a reagent mixture;
c) a means for inducing the chemical moiety to emit electomagnetic radiation; and
d) a means for detecting the emitted electromagnetic radiation.

A particularly unique and useful class of homogeneous binding assays is provided by the present invention. As described hereinbefore, these labels can be measured electrochemically by means of exposing a solution of the labeled substance of interest to an electrode. Any labeled substance which is present in the solution but cannot gain access to the surface of the electrode will not be detected. This can occur, for example, if the labeled substance is bound directly or indirectly to the surface of the reaction vessel into which the electrode is placed, or if the label is imbedded deep into the interior of the specific complex, such as Within an antigen-antibody complex, or if the electrode itself were coated with a layer through which labeled material could pass but complexed labeled material could not pass. In addition, it should be possible to coat the surface of an electrode with antibodies, so that only labeled antigen bound to the immobilized antibodies can obtain access to the electrode and thereby be determined. This particular homogenous method may be most effective if the requird electrode potential is applied in short pulses.

It is within the scope of the present invention to use a combination of means for determining the presence of labeled compounds. For example, it may be desirable to measure the total amount of labeled substance by a means which does not distinguish between bound and unbound labeled substance such as photoluminescence or chemiluminescence, and to determine the amount of bound labeled substance by a means which does distinguish between bound and unbound labeled substance, such as electrochemiluminescence, for example. Such a combination of methods could be performed on the same sample, and thus provide a richer source of information about the sample than could any method when used individually. It is also within the scope of this invention to determine the presence of two or more differently labeled compounds within the same reaction mixture. This is possible either if the labels emit electromagnetic radiation of differing wavelengths or if the labels can be induced to emit electromagnetic radiation by exposure to energy of different values or source.

This invention also provides a method of determining the presence of a chemical moiety having the formula: $(A)_k(B)_u$, wherein A is a compound which can be induced to repeatedly emit electromagnetic radiation by direct exposure to an electrochemical energy source; B is a substance which is attached to A; k is an integer equal to or greater than one; and n is an integer equal to or greater than 1. These compounds may be inorganic, organometallic or organic compounds, e.g. rubrene, 9,10-diphenyl anthracene, ruthenium-containing or osmium-containing labels, palladium and platinum complexes of alpha, beta, gamma, delta-tetraphenylporphyrin, rhenium complexes such as fac-tricarbonylchloro (1, 10-phenanthroline)-rhenium (I), molybdenum (II) halide cluster ions such as $Mo_6Cl_{14}^{2-}$, tetrakis [mudiphosphito $(2^-)$-P,P']diplatinate (II), a bis (bipyridyl) osmium diphosphine complex and a variety of laser dyes.

The method comprises forming a reagent mixture under suitable conditions containing the chemical moiety and inducing the chemical moiety to repeatedly emit electromagentic radiation by directly exposing the moiety to electrochemical energy. The emitted electromagnetic radiation is then detected by suitable methods thereby determining the presence of the chemical moiety.

Suitable conditions for this method may comprise aqueous solutions or nonaqueous solvent systems, e.g. dimethylsulfoxide, N,N'-dimethylformamide, N-methylpyrrolidinone, tert-butyl alcohol, dioxan, or tetrahydrofuran.

Biological and nonbiological substances (B) may be incorporated into the moieties by any form of attachment to A. The attachment may be by coordination to a metal atom present in A or to a ligand of A. The attachment may be through covalent, electrostatic, or hydrogen bonding. The type of linkage will be determined by the suitable chemical groups available for binding on both A and B.

Suitable substances (B) include, for example, whole cells, viruses, subcellular particles, nucleic acids, polysaccharides, proteins, glycoproteins, lipoproteins, lipopolysaccharides, lipids, fatty acids, peptides, cellular metabolites, hormones, pharmacological agents, tranquilizers, barbiturates, alkaloids, steroids, vitamins, amino acids and sugars. The substances are not limited to biological substances and may by any suitable non-biological substance such as a polymer, organic or inorganic compound.

The chemical moiety is induced to emit electromagnetic radiation by creating an excited state of the moiety which luminesces at wavelengths from about 200 nanometers to about 900 nanometers at ambient temperatures. In this embodiment of the invention the chemical moiety is excited by exposing the reagent mixture to electrochemical energy. The potential at which the reduction or oxidation of the inventive chemical moiety will occur depends upon its exact chemical structure as well as factors such as the pH of the solution and the nature of the electrode used. It is well known to those of ordinary skill in the art how to determine the optimal potential and emission wavelength of an electrochemiluminescent system. The electrochemiluminescent species may be measured by any suitable measurement such as the measurement of electric current or emitted electromagnetic radiation.

The method of determining the presence of the moiety may also be performed when the moiety is capable of binding to another chemical agent. The chemical agent may be any substance capable of binding to the moeity in a specific manner. Examples of such methods are nucleic acid hydridization techniques, antibody-antigen based techniques and enzyme-ligand techniques.

In another embodiment of the invention the presence of an analyte of interest which binds to the chemical moiety, $(A)_k(B)_u$ may be detected.

The analyte of interest may be any substance which is capable of binding to the electrochemiluminescent moiety, such as the binding of an antigen to an antibody labeled with an electrochemiluminescent moiety. The method involves contacting the analyte with the chemical moiety under suitable conditions so as to form a reagent mixture. The chemical moiety is then induced to repeatedly emit electromagnetic radiation by directly exposing the moiety to electrochemical energy. The presence of the analyte is determined by detecting the electromagnetic radiation emitted by the chemical moiety bound to the analyte.

Competitive binding methods may also be used to determine the presence of an analyte of interest wherein the analyte and the chemical moiety, $(A)_k(B)_u$, bind competitively to a complementary material. The complementary material is contacted with the chemical moiety and analyte under suitable conditions so as to form a reagent mixture. The chemical moiety is induced to repeatedly emit electromagnetic radiation by directly exposing the moiety to electrochemical energy. The presence of the analyte of interest is determined by detecting the amount of emitted electromagnetic radiation.

This invention also concerns compositions which comprise the ruthenium-containing or osmium-containing chemical moieties of this invention and one or more different chemical moieties each of which can be induced to emit electromagnetic radiation of a different distinct wavelength. These compositions are useful in methods and systems of detecting two or more different substances or analytes of interest contained in a mixture of the same and other substances.

In one embodiment of the invention, the chemical moieties are each attached to different analytes of interest.

The different chemical moiety or moieties may be any suitable chemical moiety such as inorganic, organic and organometallic compounds which can be induced to emit electromagnetic radiation, e.g. rubrene or 9,10-diphenylanthracene. These moieties may be such moieties that are induced to emit electromagnetic radiation when exposed to energy of different values or sources than the energy used to induce electromagnetic radiation from the ruthenium-containing or osmium-containing chemical moieties. In a specific embodiment of the invention, each other chemical moiety emits electromagnetic radiation of a different distinct wavelength when induced to emit electromagnetic radiation by energy of the same source and value that induces the ruthenium-containing or osmium-containing chemical moiety to emit electromagnetic radiation.

Methods for determining these chemical moieties comprise forming a reagent mixture under suitable conditions containing the chemical moieties and then inducing the chemical moieties to emit electromagnetic radiation by exposing the reagent mixture to chemical energy or electrochemical energy. The presence of each of the moieties is determined by detecting the electromagnetic radiation of different wavelengths emitted by each of the moieties.

The invention also concerns a method of determining the presence of one or more analytes of interest which bind selectively to the different chemical moieties present in the same mixture. The method comprises contacting the analytes with the chemical moieties under suitable conditions so as to form a reagent mixture. The moieties are induced to emit electromagnetic radiation by exposing the reagent mixture to chemical energy or electrochemical energy and the emitted electromagnetic radiation of different wavelengths is detected to determine the presence of each of the analytes of interest.

These methods in which the presence of two or more chemical moieties is determined in a mixture are applicable to all instances described previously for determining the ruthenium-containing and osmium-containing luminescent labels. This embodiment, however, allows for the determination of two or more different substances present in the same sample simultaneously.

Also provided are systems for determining the presence of one or more different chemical moieties or analytes of interest which bind to the chemical moieties, each of which may be induced to emit electromagnetic radiation of a different wavelength. In one embodiment of the invention, each moiety is attached to a different analyte of interest.

In another embodiment of the invention the different chemical moieties are induced to emit electromagnetic radiation by exposure to energy of different values or different sources. The methods of determining these different chemical moieties are essentially the same as those for determining the chemical moieties which emit different wavelengths of electromagnetic radiation, except for the induction step. These chemical moieties are induced to emit electromagnetic radiation by energy of different values or sources. The sample containing the moieties is exposed to each of the different energy values or sources at a different time and the electromagnetic radiation emitted by the specific moiety is detected, thus determining the presence of the moiety.

This method is also useful for determining the presence of analytes of interest which bind selectively to the different chemical moieties present in the sample.

A multiplicity of chemical moieties of the present invention may be determined by:

a) forming a reagent mixture under suitable conditions containing the chemical moieties;

b) inducing the chemical moieties to emit electromagnetic radiation at different times by exposing the reagent mixture at different times to energy of different values or from different sources; and c) detecting the emitted electromagnetic radiation after exposing the mixture to each of the different values or different sources of energy and thereby determining the presence of each of the chemical moieties.

Another embodiment of the invention involves methods and systems of determining one or more different electrochemiluminescent moieties of the formula $(A)_k(B)_u$ present in the same sample. These chemical moieties contain different compounds which emit electromagnetic radiation of different wavelengths when exposed to an electrochemical energy source or can each be induced to emit electromagnetic radiation by exposure to distinct electrochemical energy sources. These different electrochemiluminescent moieties may be specifically attached to different substances or analytes of interest. Determination of the different moieties involves the same procedures as discussed previously.

This invention is illustrated in the examples which follow. The examples are set forth to aid in an understanding of the invention but are not intended to, and should not be contrued to, limit in any way the invention as set forth in the claims which follow thereafter.

EXAMPLE I

Preparation of Ruthenium bis (2,2'-bipyridine) (2,2'-bipyridine-4,4'-dicarboxylic Acid) bis (hexafluorophosphate)

Sodium bicarbonate (0.40 g), ruthenium dichlorobis(2,2'-bipyridine) (0.40 g), and 2,2'-bipyridine-4,4'-dicarboxylic acid (0.30 g) were stirred in refluxing methanol (20 ml)-water (5 ml) for 9 hours. The resulting solution was cooled in an ice bath, treated with 5 drops concentrated $H_2SO_4$, and allowed to stand at ice temperature for 1.5 hours. A precipitate formed, which was separated by filtration and washed with MeOH (8 ml).

The combined filtrate and wash solution were treated with a solution of sodium hexafluorophosphate (5.0 g) in water (25 ml). The resulting solution was cooled in an ice bath for 3 hours, and the resulting precipitate of red-purple crystals was collected by filtration (0.40 g).

EXAMPLE II

Preparation of Active Ester of Ruthenium bis (2,2'-bipyridine) (2,2'0bipyridine-4,4'-dicarboxylic Acid)

Dicyclohexylcarbodiimide (DCC, 0.046 g) and N-hydroxysuccinimide (0.034 g) were dissolved in DMF (2 ml) with stirring, and cooled in an ice bath. A solution of ruthenium bis (2,2'-bipyridine) (2,2'-bipyridine-4,4'-dicarboxylic acid) (0.101 g, prepared as in Example I) dissolved in DMF (1 ml) was added, and the mixture was stirred 5 hours at ice bath temperature. A precipitate formed and was separated by centrifugation. The supernatant containing the activated ruthenium complex was retained for labelling of substrates.

EXAMPLE III

Labelling of Bovine Serum Albumin (BSA) With Activated Ruthenium Complex

The DMF solution of activated ruthenium complex prepared in Example II (1 ml) was added to a stirred solution of BSA in aqueous Physiologic Buffered Saline (PBS, 5 ml; 25 mg/ml BSA). The mixture was stirred overnight, and precipitate was removed by centrifugation. The supernatant containing ruthenium-labelled BSA was analyzed by two methods.

METHOD 1

Dialysis

Ruthenium-labelled BSA solution was dialyzed with PBS solution. As a control, the unbound, activated ruthenium complex prepared in Example II was also dialyzed with PBS solution. After 8 hours, the control showed no fluorescent species within the dialysis tube. The ruthenium labelled BSA solution, however, showed strong fluorescence, indicating that the ruthenium complex was bound to the high molecular weight BSA.

METHOD 2

Microfiltration

Ruthenium-labelled BSA solution was placed in an Amicon microconcentrator and centrifuged at 8000 rpm. A small fraction of red-orange solution remained above the filter, and this colored fraction was diluted with wash PBS solution and centrifuged. This procedure was repeated several times. After the fourth wash, colorless solution passed through the filter, while highly red-orange colored material remained above the filter. This result indicates that the ruthenium complex was bound to the high molecular weight BSA.

EXAMPLE IV

Labelling of Human Immunoglobulin G (IgG) With Activated Ruthenium Complex

The DMF solution of activated ruthenium complex prepared in Example II was added to a stirred solution of affinity purified human IgG in aqueous buffer. The ruthenium labelled IgG solution fluoresced brightly after extensive dialysis, indicating that the ruthenium complex was bound to the high molecular weight affinity purified human IgG.

EXAMPLE V

Labelling of Rabbit Anti-salmonella Antibody

The DMF solution of activated ruthenium complex prepared in Example II (0.1 ml) was stirred with rabbit serum containing anti-Salmonella antibody (1 mi) at room temperature for 1 hour, and then quenched by addition of diethanolamine (0.1 ml). Salmonella cells were treated with the resultant solution containing ruthenium labelled anti-Salmonella antibody. The cells were separated by centrifugation and resuspended in fresh buffer five times, in order to separate the cells from any unbound antibody (including ruthenium labelled unbound antibody) and from any free ruthenium complex. The Salmonella cells, treated with ruthenium labelled anti-Salmonella antibody, emitted bright red-orange light when viewed on a fluorescence optical microscope, indicating that the anti-Salmonella antibody was labelled with ruthenium complex, and that the ruthenium labelled antibody retained its ability to bind to Salmonella cells under conditions where the ruthenium complex fluoresced.

EXAMPLE VI

The procedure of Example V was repeated using normal mouse serum (i.e., lacking anti-Salmonella antibody) in place of rabbit serum containing anti-Salmonella antibody. The Salmonella cells, after treatment, did not emit red-orange light when viewed on a fluorescence optical microscope, indicating that non-specific binding of ruthenium labelled normal mouse serum components to Salmonella cells did not occur.

EXAMPLE VII

Labelling of Goat Anti-Rabbit Immunoglobulin (IgG) and Comparison With Rhodamine The DMF solution of activated ruthenium complex prepared in Example II was added to a stirred solution of affinity purified goat anti-rabbit IgG. After reaction, the mixture was dialyzed against buffer. Material remaining in the dialysis tube fluoresced under UV light.

The ruthenium labelled IgG was tested for reactivity toward Salmonella coated with rabbit anti-Salmonella antibodies. Rabbit anti-Salmonella antibodies were reacted *Salmonella worthington* that had been fixed to a glass microscope slide, and unreacted antibody was washed away with buffer. The ruthenium labelled goat anti-rabbit IgG was then reacted with the antibody treated *S. worthington*, and unreacted material was washed away with buffer. The slide was examined under an optical microscope equipped with a 50 W mercury lamp, and very bright orange-red fluorescence was observed on and around the bacterium.

A control experiment tested for non-specific binding of ruthenium-labelled antibody. *S. worthington*, fixed to a glass microscope slide, was reacted with normal mouse serum, and then with ruthenium labelled goat anti-rabbit IgG antiserum. The same washing procedures were followed. No orange-red fluorescence was observed.

For comparison purposes, a rhodamine isothiocyanate conjugated goat anti-rabbit IgG antiserum (at a protein concentration equivalent to the ruthenium-conjugated antibody) was reacted with *S. worthington* coated with rabbit anti-Salmonella antibodies. Red fluorescence was barely detectable and the intensity of fluorescence was significantly less than the ruthenium conjugate.

EXAMPLE VIII

Electrochemiluminescent (ECL) Detection of Ruthenium Labelled Bovine Serum Albumin (BSA)

ECL measurements were carried out in a one compartment cell (30 ml) with an optically flat bottom. The working electrode was glassy carbon, the counter electrode was platinum gauze, and the pseudo-reference electrode was a silver wire. Light intensity measurements were made by applying a potential of −2.0v (versus the Ag wire), detecting the emitted light with a photomultiplier tube (Hamamatsu 928), and integrating the resulting signal for 2 s with a Bascom-Turner Recorder.

Acetonitrile-water (9 ml, 50:50 v/v), tetrabutylammonium tetrafluoroborate (329 mg), and diammonium peroxydisulfate (42 mg) were mixed in the ECL cell, and background light intensity was recorded. Ruthenium labelled BSA solution (prepared in Example III) was diluted in acetonitrile-water (50:50 v/v) and the diluted BSA solution (1 ml) was added to the ECL cell. The resulting solution was deaerated by bubbling solent-saturated nitrogen. Table I summarizes results for different concentrations of ruthenium labelled BSA.

TABLE I

| Light Intensity (Arbitrary Units) | (Ruthenium) M |
|---|---|
| 5.2 | blank |
| 20.63 | $1 \times 10^{-11}$ |
| 33.25 | $1 \times 10^{-10}$ |
| 54.42 | $9 \times 10^{-10}$ |
| 150.2 | $8 \times 10^{-9}$ |

EXAMPLE IX

Preparation of 4,4'-(dichloromethyl)-2,2'-bipyridyl bis(2,2' bipyridyl) Ruthenium (II)

4,4'-Diethoxycarbonyl-2,2'-bipyridine was prepared from 2,2-bipyridine-4,'dicarboxylic acid by the method of Sprintschink et al. (J. Amer. Chem. Soc. 99, 4947 (1977)). The diethyl ester (100 mg) was dissolved in anhydrous diethyl ether (35 ml). Lithium aluminum hydride (100 mg) was added, and following a 30 minute incubation diethyl ether (35 ml) and ice cold deionized water (100 ml) were added. The solution was mixed throughly and the ether layer collected. The aqueous phase was extracted twice more with ether (70 ml). The combined ether extracts were dried over anhydrous sodium sulfate and filtered. The solvent was removed on a rotary evaporator to give the desired product (43 mg). This 43 mg of 4,4-Di(hydroxymethyl)-2,2'-bipyridine and 120 mg of cisdichloro bis (2,2'-bipyridine) ruthenium (II) dihydrate were added to ethanol (25 ml), and the solution was refluxed for 14 hours. After the solution had cooled, 50 ul of solution of ammonium hexafluorophosphate (1 gm in 1 ml of water) was added, the resultant crystalline solid was collected, washed with a small volume of ethanol and dried to give 138 mg of the hexafluorophosphate salt of the 4,4-dihydroxymethyl complex. This complex (6 mg) was added to thionyl chloride (5 ml), and the solution was refluxed for 6 hours. The thionyl chloride was removed by distillation, and the solid residue was dissolved in a dioxane-water (1:1) mixture (500 ul). This solution containing 4,4'-(dichloromethyl)-2,2'-bipyridyl, bis(2,2' bipyridyl) ruthenium (II) was used for labeling of antibody.

EXAMPLE X

Labeling of Rabbit and Sheep Anti-Mouse IgG With 4,4'-(dichloromethyl)-2,2'-bipyridyl, bis(2,2' bipyridyl) Ruthenium (II)

The rabbit and sheep antibodies were received as 2 mg/ml solutions in PBS. These solutions were dialyzed overnight against sodium bicarbonate (500 ml, 50 mM, pH9). The 10 antibody (2 mg) was then diluted with sodium bicarbonate solution to give a final volume of 2 ml. This solution (1 ml) was added to sodium carbonate solution (1 ml, 50 mM) to adjust the pH to 10. The solution of activated complex in dioxane-water (100 ul) was added to the solution of antibody and allowed to react at 4° C. for 16 hours. After this, BSA (5 mg) was added to the reaction, and the solution was immediately dialyzed against carbonate buffer (500 ml, 25 mM, pH9). The dialysis buffer was changed three times at 24 hour intervals.

EXAMPLE XI

Demonstration of Immunological Reactivity of Labeled Rabbit and Sheep Anti-Mouse Immunoglobulin by Fluorometric Analysis A formalinized suspension of *Legionella pneumophila* 1 (Philadelphia 1 isolate) was adjusted to an optical density (at 425 nm) of 1.00 by dilution with PBS buffer. A 1.3 dilution (1 ml) of this suspension was added to a series of conical microcentrifuge tubes. The cells were centrifuged (10 minutes, 10,000 RPM), the supernatant was decanted, and the cells were resuspended in a 1:100 dilution in PBS (1 ml) of a mouse monoclonal IgG antibody ("10C8", 0.85 mg/ml) or in PBS as a negative control. After incubation at room temperature for 1 hour, the cells were centrifuged as before, the supernatant was decanted, the cells were resuspended in PBS buffer and centrifuged again. Following decantation of the supernatant, the cells were resuspended in a 1:5 dilution (in PBS) of the pooled ruthenium labeled rabbit and sheep anti-mouse IgG Antibody (1 ml, 10 mg ruthenium complex/ml), or in a 1:50 dilution (in PBS) of fluorescein labeled goat anti-mouse IgG antibody (1 ml, 0.5 mg IgG/ml) as a positive control, or in PBS as a negative control. After incubation at room temperature for 1 hour, the cells were centrifuged as before, the supernatant was decanted, and the cells resuspended in PBS and washed twice, with centrifugation, as before. Following the last wash the cells were resuspended in PBS (1 ml) and transferred to a polystyrene cuvette for fluorometric analysis.

Excitation and emission scans of the fluorescein labeled goat anti-mouse IgG antibody solution showed an excitation peak at 491 nm and an emission peak at 519 nm. These wavelengths were used for the fluorescence measurements of the fluorescein labeled cells. Excitation and emission scans of the ruthenium labeled rabbit/sheep anti-mouse IgG antibody solution showed an excitation peak at 455 nm and an emission peak at 623 nm. These wavelengths were used for the fluorescence measurements of the ruthenium labeled cells. Cell suspensions which had been incubated with PBS instead of primary "10C8" antibody and fluorescent conjugate served as negative controls and were used to blank the fluorometer. The fluorescence of cell suspensions which had been incubated with both primary "10C8" antibody and fluorescent conjugate was defined as 100, and all other fluorescence measurements were made in fluorescence units relative to these internal standards. Table II summarizes the results, which demonstrate that the ruthenium labeled anti-mouse IgG conjugate fluoresces and exhibits specific immunological reactivity in the presence of primary "10C8" antibody.

TABLE II

RELATIVE FLUORESCENCE UNITS

| | Fluorescein (at 519 nm) 1:3 cell Dilution | Ruthenium (at 623 nm) 1:3 cell Dilution |
|---|---|---|
| Fluorescence of conjugate with primary antibody | ≡100 | ≡100 |
| Fluorescence of conjugate without primary antibody | 37 | 64 |
| Background fluorescence (with primary antibody, without conjugate) | 6 | 48 |

EXAMPLE XII

Electrochemiluminescence in Various Organic Solvents

The electrochemiluminesence of tris (2,2'-bipyridyl) ruthenium (II) chloride hexahydrate was measured in a 15 ml three-neck, round bottom flask containing 10 ml of a solution prepared as described below; a 1.5 mm×10 mm magnetic stir bar; a 1.0 mm diameter silver wire quasi-reference electrode; a combination 28 gauge platinum wire counter electrode; and a working electrode consisting of a 22 gauge platinum wire welded to a 1 cm×1 cm square piece of 0.1 mm thick, highly polished platinum foil. (The working platinum foil electrode was shaped into a 3/16 of an inch diameter semi-circle surrounding the 28 gauge platinum wire counter electrode by 3/32 of an inch equidistantly.)

The silver wire was connected to the EG&G Model 178 electrometer probe of the EG&G Model 173 potentiostat/galvanostat. The platinum wire counter electrode and the platinum working electrode were connected to the anode and cathode respectively of the EG&G Model 173 potentiostat. The device was grounded.

Cyclic voltammetry was performed with the EG&G Model 173 potentiostat to which an EG&G Model 175 universal programmer was attached. The programmer was set for 100 mV/second sweeps between +1.75 volt anodic and −1.80 volt cathodic potentials. Electrochemiluminescence was detected using a Hamamatsu R928 photomultiplier tube, set inside a Products for Research Model PR1402RF photomultiplier tube housing which was fitted with a Kodak #23A gelatin (red) filter. The photomultiplier tube housing was connected to an Oriel Model 7070 photomultiplier detection system. The cyclic voltammogram was recorded on a Houston Instruments Model 200 X-Y recorder.

Cyclic voltammograms were generated for 1 mM tris (2,2'-bipyridyl) ruthenium (II) chloride hexahydrate (Aldrich Chemical Company), 0.1M tetrabutylammonium tetrafluoroborate ($TBABF_4$) (.Aldrich Chemical Company) solutions prepared with the following spectroscopic grade organic solvents: acetonitrile; N-dimethylformamide; dimethylsulfoxide and 1-methyl, 2-pyrrolidinone (Aldrich Chemical Company). Tert-butyl alcohol and deionized, distilled water (1:1, v/v) also was used to make a solution containing 1 mM tris (2 ,2'-bipyridyl) ruthenium (II) chloride hexahydrate and 0.1M $TBABF_4$. The resulting voltammograms did not indicate any change in the redox potential of the tris (2,2'-bipyridyl) ruthenium (II) chloride upon variation of the organic solvent.

For visual observation of electrochemiluminescence, solutions were prepared as follows: sufficient amounts of tris (2,2'-bipyridyl) ruthenium (II) chloride hexahydrate and TBABF$_4$ were dissolved in the spectroscopic grade organic solvents described above to provide final concentrations of 1M and 0.1M, respectively. 10 ml of the resulting solution was then added to the 15 ml three-neck, round bottom flask. The electrodes were immersed in the solution and the working electrode pulsed between a +1.75 and −1.45 volt potential to generate electrochemiluminescence. Electrochemiluminescence was visually observed in each of the solutions described above.

For quantitative measurements of the effect of solvent variation on electrochemiluminescence, solutions were prepared as follows: sufficient amounts of tris (2,2'-bipyridyl) ruthenium (II) chloride hexahydrate TBABF$_4$ were added to the organic solvents described above to provide final concentrations of 2 mm and 0.2M respectively. To an aliquot of this solution was added an equal volume of deionized, distilled water containing a strong oxidizing agent, ammonium persulfate, at a concentration of 36 mM. Control solutions that did not contain the tris (2,2'-bipyridyl) ruthenium (II) chloride hexahydrate were prepared. 10 ml of the resulting solution was then added to the 15 ml three-neck round bottom flask. Electrochemiluminescence was accomplished by pulsing for one second intervals.

Electrochemiluminescent measurements were performed by integrating the resulting electrochemiluminescent photomultiplier tube signal using an integrator connected to a Micronta Model 22191 digital multimeter. The electrochemiluminescent signal was integrated for 10 seconds during the pulsing and recorded in millivolts. The results are shown in Table III and indicate that variation of solvents effects quantum efficiency of the ruthenium (II) chloride.

TABLE III

| Organic Solvent | Tris RuBiPy ($10^{-6}$M) | Control | Δ |
|---|---|---|---|
| Acetonitrile | 2,540* | 104 | 2,436 |
| tert-butyl alcohol | 1,280 | 0 | 1,280 |
| N, N dimethyl-formamide | 2,390 | 143 | 2,247 |
| Dimethylsulfoxide | 2,760 | 29 | 2,731 |
| 1-methyl-2-pyrrolidinone | 1,630 | 0 | 1,630 |

*all measurements in millivolts.

EXAMPLE XIII

Sensitivity of Detection of Electrochemiluminescence of Ruthenium-Labeled Rabbit Anti-Mouse Immunoglobulin G (IgG) Antibody The electrochemiluminescence of rabbit anti-mouse IgG antibody labeled with 4,4-(dichloromethyl)-2,2-bipyridyl, bis(2,2-bipyridiyl) ruthenium (II) (ruthenium-labeled rabbit anti-mouse IgG antibody) was measured in a 15 ml three-neck, round bottom flask containing 10 ml of a solution prepared as described below; a 1.5 mm×10 mm magnetic stir bar; a 1.0 mm diameter silver wire quasi-reference electrode; a combination 28 gauge platinum wire counter electrode, and a working electrode consisting of a 22 gauge platinum wire welded to a 1 cm×1 cm square piece of 0.1 mm thick, highly polished platinum foil. (The working platinum foil electrode was shaped into a 3/16 of an inch diameter semicircle surrounding the 28 gauge platinum wire counter electrode by 3/32 of an inch equidistantly.)

The silver wire was connected to the EG&G Model 178 electrometer probe of the EG&G Model 173 potentiostat/galvanostat. The platinum wire counter electrode and the platinum working electrode were connected to the anode and cathode respectively of the EG&G Model 173 potentiostat. The device was grounded.

The electrochemiluminescence emitted from the ruthenium-labeled rabbit anti-mouse IgG antibody solution was detected using an Hamamatsu R928 photomultiplier tube, set inside a Products for Research Model PR1402RF photomultiplier tube housing which was fitted with a Kodak #23A gelatin (red) filter. The photomultiplier tube housing was connected to an Oriel Model 7070 photomultiplier detection system.

Electrochemiluminescence was induced by pulsing for one second intervals, between zero and −2.0 volts cathodic potential. Electrochemiluminescent measurements were performed by integrating the resulting electrochemiluminescent photomultiplier tube signal using an integrator connected to a Micronta Model 22191 digital multimeter. The electrochemiluminescent signal was integrated for 10 seconds during the pulsing and recorded in millivolts.

A stock solution of $1.25 \times 10^{-7}$M ruthenium-labeled rabbit anti-mouse IgG antibody was prepared from a concentrated solution (2 mg/ml, 7.5 Ru/antibody) of the labeled antibody by dilution in phosphate-buffered saline (PBS). An aliquot of this solution (80 microliters) was added to 10 ml of dimethylsulfoxide (DMSO)/deionized, distilled water (1:1) containing 0.1M tetrabutylammonium tetrafluoroborate (TBABF$_4$) and 18 mM ammonium persulfate in the reaction vessel. The final ruthenium-labeled antibody concentration was $1 \times 10^{-9}$M. Electrochemiluminescence was measured as described above.

Additional solutions representing various dilutions of the ruthenium-labeled rabbit anti-mouse IgG antibody stock solution were made and aliquots (80 microliters) of these solutions were added to the same solution of ruthenium-labeled antibody in the reaction vessel in increments which resulted in the following concentrations of labeled antibody: $5 \times 10^{-9}$M, $1 \times 10^{-8}$M, and $5 \times 10^{-8}$M. Electrochemiluminescence measurements were made for each solution as described. These measurements are listed in Table IV below. These results indicate the sensitivity of electrochemiluminescent detection of labeled antibody ($1 \times 10^{-9}$M), and the dependence of the intensity of electrochemiluminescence on the concentration of the ruthenium-labeled anti-mouse IgG antibody.

TABLE IV

ELECTROCHEMILUMINESCENCE (ECL) OF RUTHENIUM-LABELED RABBIT ANTI-MOUSE IMMUNOGLOBULIN G (IgG) ANTIBODY

| Concentration of Ruthenium-Labeled Anti-Mouse IgG Antibody | ECL (mV) |
|---|---|
| $5 \times 10^{-8}$M | 1610 |
| $1 \times 10^{-8}$M | 892 |
| $5 \times 10^{-9}$M | 418 |
| $1 \times 10^{-9}$M | 72 |
| 0 | 0 |

EXAMPLE XIV

Immunological Reactivity of Ruthenium-Labeled Bovine Serum Albumin (BSA) In a Solid Phase Enzyme-Linked Immunosorbent Assay (ELISA)

The wells of a polystyrene microtiter plate were coated with a saturating concentration of either bovine serum albumin labeled with 4,4-(dichloromethyl)-2,2-bipyridyl, bis(2,2-bipyridyl) ruthenium (II), i.e. ruthenium-labeled bovine serum albumin, (6 Ru/BSA, 20 micrograms/ml in PBS buffer, 50 microliters/well) or unlabeled BSA (20 micrograms/ml in PBS buffer, 50 microliters/well) and incubated for one hour at room temperature. After this incubation period the plate was washed three times with PBS, 5 minutes per wash. A solution containing 6 mg/ml rabbit anti-BSA antibody was diluted 1:20,000, 1:30,000, 1:40,000, 1:50,000, and 1:60,000 in PBS, and the dilutions were added in duplicate to the wells coated with ruthenium-labeled BSA or unlabeled BSA, and the plate was incubated for one hour at room temperature. After three washes with PBS as before, the presence of bound rabbit anti-BSA antibody was determined by adding goat anti-rabbit IgG-peroxidase conjugate (1:1000 dilution in PBS of a 0.5 mg/ml solution, 50 microliters/well) to each well and incubating the plate for one hour at room temperature. After washing the plate twice with PBS, 0.5% Tween-20, and twice with PBS as before, hydrogen peroxide (30%) and 2,2'-azino-di-[3-ethyl-benzthiazoline sulfonate] (KPL, Gaithersburg, Md.) were mixed in equal volumes and 200 microliters were added to each well of the plate. After a 30 minute incubation at room temperature, the plate was read spectrophotometrically at 414 nm. The mean background absorbence in the control wells was subtracted from the mean value of duplicate readings for each dilution of the rabbit anti-BSA antibody that was added to the wells coated with ruthenium-labeled BSA or unlabeled BSA. These corrected absorbence values are shown in Table V.

The curves obtained for the unlabeled BSA and ruthenium-labeled BSA were parallel, with corrected absorbance values at each point on the two curves at a constant ratio, approximately 0.6. Identical results were obtained for two other lots of ruthenium-labeled BSA which were made using the same activated ruthenium complex as described previously, and which had similar Ru/BSA labeling ratios. These results indicate that the ruthenium-labeled BSA is immunologically reactive and that it retains approximately 60% of its immunoreactivity when labeled with ruthenium in comparison to unlabeled BSA.

TABLE V

| Rabbit Anti-BSA Antibody Dilution | ABSORBANCE AT 414 nm | | Relative Immunoreactivity |
|---|---|---|---|
| | Unlabeled BSA | Ruthenium-labeled BSA | |
| 20,000 | 1.06 | 0.66 | 62% |
| 30,000 | 0.83 | 0.50 | 60% |
| 40,000 | 0.67 | 0.40 | 60% |
| 50,000 | 0.56 | 0.33 | 59% |
| 60,000 | 0.47 | 0.28 | 60% |

EXAMPLE XV

Immunological Reactivity of Ruthenium-Labeled Rabbit Anti-Mouse Immunoglobulin (IgG) Antibody by a Competitive Solid Phase Enzyme Linked-Immunosorbent Assay Rabbit anti-mouse IgG antibody labeled with 4,4-(dichloromethyl)-2,2-bipyridyl, bis(2,2-bipyridyl) ruthenium (II) (ruthenium-labeled rabbit anti-mouse IgG antibody) was compared with unlabeled rabbit anti-mouse IgG antibody with respect to its ability to compete with enzyme-labeled, anti-mouse IgG antibody for binding to mouse IgG. The wells of a 96-well polystyrene microtiter plate were coated with a solution of mouse IgG (5 micrograms/ml in PBS buffer), incubated for 60 minutes at room temperature and washed three times, 5 minutes per wash, with PBS. Two solutions were prepared, one containing a mixture of rabbit anti-mouse IgG-alkaline phosphatase conjugate and rabbit anti-mouse IgG (1 mg/ml), and the other a mixture of rabbit anti-mouse IgG-alkaline phosphatase conjugate and ruthenium-labeled rabbit anti-mouse IgG (1 mg/ml, 7.5 Ru/antibody). These two solutions, and a third containing rabbit anti-mouse IgG-alkaline phosphatase conjugate, were diluted 1:6000, 1:7000, 1:8000, 1:9000, 1:10,000, 1:12,000, 1:14,000 and 1:16,000 in PBS containing 0.5% Tween-20, and added (50 microliters/well) to separate rows of the plate containing bound mouse IgG. The plate was incubated for 60 minutes at room temperature and washed twice with PBS-Tween-20 and twice with PBS, 5 minutes per wash. The enzyme substrate p-nitrophenyl phosphate (1.5 mg/ml in 10% diethanolamine buffer, pH 9.6) was added to each well (200 microliters/well); the plate was incubated for 30 minutes at room temperature and read spectrophotometrically at 405 nm. The mean background absorbance in the control well s was subtracted from the mean value of duplicate readings for each of the three solutions at each dilution. These absorbance values are shown in Table VI.

Three parallel curves were obtained, the top curve representing the uninhibited binding of the enzyme conjugate, and the two lower curves representing inhibition by ruthenium-labeled anti-mouse IgG and unlabeled anti-mouse IgG. The ruthenium-labeled, anti-mouse IgG curve, on a point-by-point comparison, approximately 81% as low as the unlabeled anti-mouse IgG curve in comparison to the enzyme conjugate curve. These results indicate that the ruthenium-labeled, anti-mouse IgG antibody is immunologically reactive for its antigen (mouse IgG), and is approximately 81% as effective as unlabeled anti-mouse IgG antibody in competing with enzyme-labeled, anti-mouse IgG antibody for binding to mouse IgG.

TABLE VI

| | ABSORBANCE AT 405 nm | | | |
|---|---|---|---|---|
| Dilution | A Anti-Mouse IgG Alkaline Phosphatase (Enzyme Conjugate) | B Enzyme Conjugate + Ruthenium Labeled Anti-Mouse IgG | C Enzyme Conjugate + Unlabeled Anti-Mouse IgG | Comparative* Degree of Inhibition |
| 6,000 | 1.48 | 0.94 | 0.79 | 77% |
| 7,000 | 1.33 | 0.82 | 0.69 | 79% |
| 8,000 | 1.21 | 0.72 | 0.62 | 82% |
| 9,000 | 1.10 | 0.65 | 0.56 | 84% |
| 10,000 | 1.01 | 0.60 | 0.51 | 82% |
| 12,000 | 0.87 | 0.51 | 0.43 | 80% |
| 14,000 | 0.77 | 0.45 | 0.37 | 81% |
| 16,000 | 0.68 | 0.40 | 0.33 | 80% |

*(A − B/A − C) × 100%

EXAMPLE XVI

Electrochemiluminescence of Ruthenium-Labeled Bovine

A solution containing $7.8 \times 10^{-6}$M bovine serum albumin (BSA) labeled with 4,4'-(dichloromethyl)-2,2'-bipyridyl, bis (2,2' bipyridyl) ruthenium (II) (ruthenium-labeled bovine serum albumin) was prepared from a stock solution of ruthenium-labeled BSA (2.6 mg/ml, 6 Ru/BSA) by dilution in phosphate-buffered saline. 26 microliters of this solution were added to 10 ml of DMSO/deionized, distilled water (1:1) containing 0.1M TBABF$_4$ and 18 mm ammonium persulfate in the reaction vessel. The final ruthenium-labeled BSA concentration was $2 \times 10^{-8}$M. Electrochemiluminescence was measured as described in Example XIII.

In an analogous manner, a solution containing $7.8 \times 10^{-6}$M unlabeled BSA was prepared and added to the reaction vessel to give a final unlabeled BSA concentration of $2 \times 10^{-8}$M. The electrochemiluminescence of this solution and of a similar solution without BSA was measured. Electrochemiluminescence measurements are shown in Table VII for covalently coupled, ruthenium-labeled BSA and unlabeled BSA.

TABLE VII

ELECTROCHEMILUMINESCENCE (ECL) OF RUTHENIUM-LABELED BSA

| Solution | ECL (mV) |
| --- | --- |
| $2 \times 10^{-8}$M Ruthenium-Labeled BSA | 730 |
| $2 \times 10^{-8}$M BSA | 100 |
| DMSO: H$_2$O (1:1) | 0 |

EXAMPLE XVII

Electrochemiluminescence of Ruthenium-Labeled Rabbit Anti-Mouse Immunoglobulin G (IgG) Antibody A solution containing $1.25 \times 10^{-6}$M rabbit anti-mouse IgG antibody labeled with 4,4'-(dichloromethyl)-2,2'-bipyridyl, bis(2,2'-bipyridyl) ruthenium (II) (ruthenium-labeled, rabbit anti-mouse IgG antibody) was prepared from a stock solution of ruthenium-labeled, rabbit anti-mouse IgG antibody (2 mg/ml, 7.5 Ru/antibody) by dilution in phosphate-buffered saline. 80 microliters of this solution were added to 10 ml of DMSO/deionized, distilled water (1:1) containing 0.1M TBABF$_4$ and 18 mM ammonium persulfate in the reaction vessel. The final ruthenium-labeled antibody concentration was $1 \times 10^{-8}$M. Electrochemiluminescence was measured as described in Example XIII.

In an analogous manner, a solution containing $1.25 \times 10^{-6}$M unlabeled, rabbit anti-mouse IgG antibody was prepared and added to the reaction vessel to give a final unlabeled antibody concentration of $1 \times 10^{-8}$M. The electrochemiluminescence of this solution and of the solution without added antibody was also measured as described. Electrochemiluminescent measurements are shown in Table VIII for covalently-coupled, ruthenium-labeled rabbit anti-mouse IgG antibody and unlabeled rabbit anti-mouse IgG antibody.

TABLE VIII

ELECTROCHEMILUMINESCENCE (ECL) OF RUTHENIUM-LABELED RABBIT ANTI-MOUSE IMMUNOGLOBULIN G (IgG) ANTIBODY

| Solution | ECL (mV) |
| --- | --- |
| $1 \times 10^{-8}$M Ruthenium Labeled Rabbit Anti-Mouse IgG Antibody | 892 |
| $1 \times 10^{-8}$M Rabbit Anti-Mouse IgG Antibody | 0 |
| DMSO: H$_2$O (1:1) | 0 |

What is claimed is:

1. A chemical compound having the formula

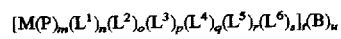

wherein:

M is ruthenium or osmium;

P is a polydentate ligand of M;

$L^1$, $L^2$, $L^3$, $L^4$, $L^5$ and $L^6$ are ligands of M, each of which is the same as or different from each other ligand;

B is a substance covalently bound to one or more of P, $L^1$, $L^2$, $L^3$, $L^4$, $L^5$ or $L^6$ through one or more amide or amine linkages;

m is an integer equal to or greater than 1;

each of n, o, p, q, r and s is zero or a positive integer;

t is an integer equal to or greater than 1; and u is an integer equal to or greater than 1;

P, $L^1$, $L^2$, $L^3$, $L^4$, $L^5$, $L^6$ and B being of such composition and number that the chemical compound can be induced to emit electromagnetic radiation and the total number of bonds to M provided by the ligands of M equals the coordination number of M.

2. A chemical species having the structure

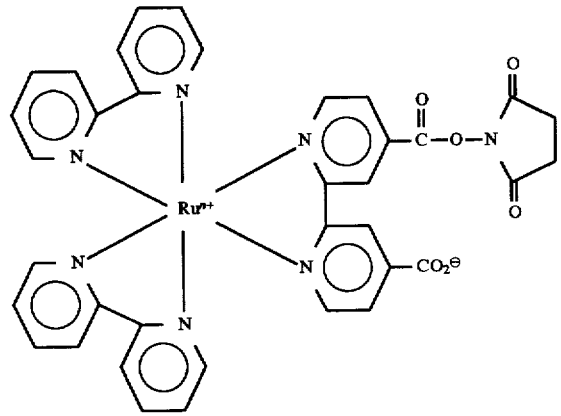

wherein n is the integer 1, 2, or 3.

3. A chemical species having the structure

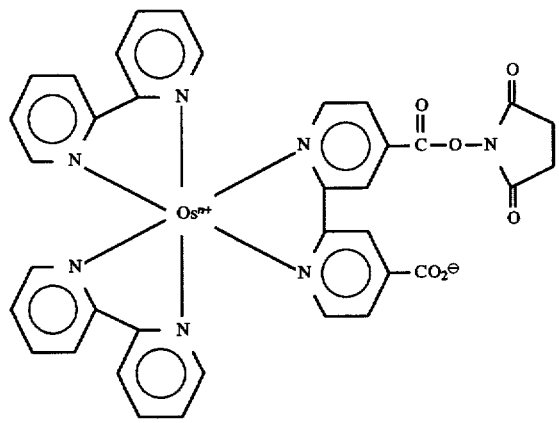

wherein n is the integer 1, 2 or 3.

4. A chemical species having the structure

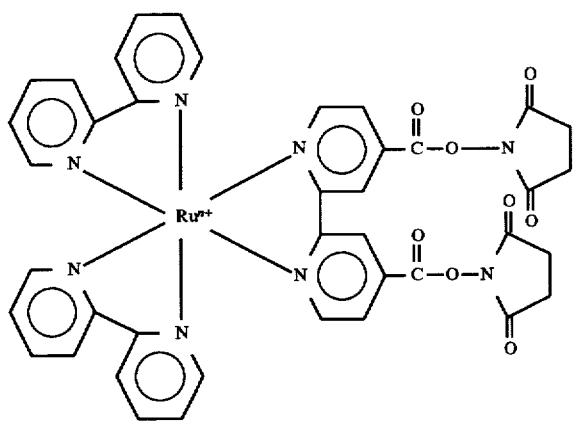

wherein n is the integer 1, 2, or 3.

5. A chemical species having the structure

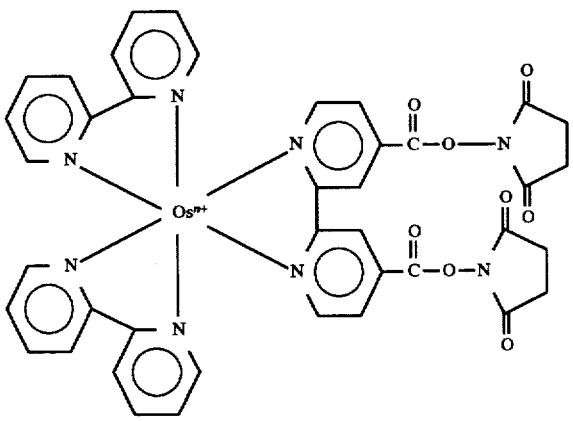

wherein n is the integer 1, 2 or 3.

6. A chemical species having the structure

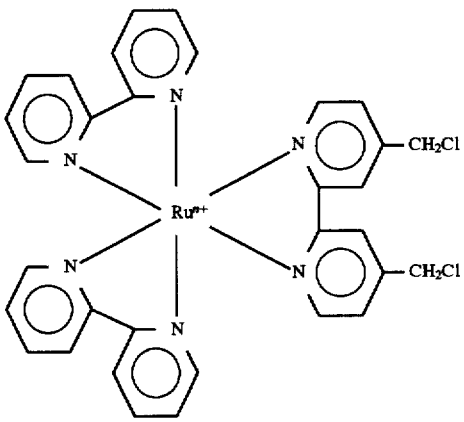

wherein n is the integer 1, 2 or 3.

7. A chemical species having the structure

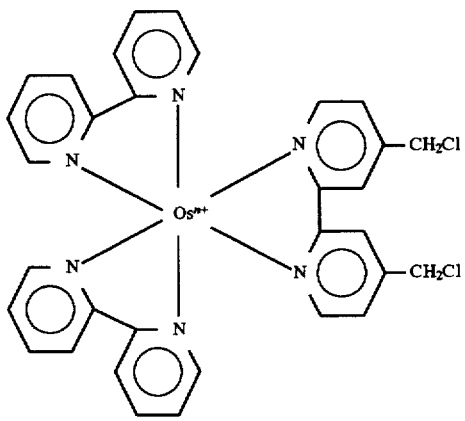

wherein n is the integer 1, 2 or 3.

8. A salt comprising a chemical species according to any of claims 2, 3, 4, 5, 6 or 7 and a counterion.

9. A salt according to claim 8 wherein the counterion is a cation selected from the group consisting of $NH_4^+$, guanidinium, $Ag^+$, $Li^+$, $Na^+$, $K^+$, $Ca^{2+}$, $Mg^{2+}$, $Mn^{2+}$ or $Cd^{2+}$, or an anion selected from the group consisting of $SO_4^{2-}$, a halide, carbonate, hexafluorophosphate or tetrafluoroborate.

10. A compound having the structure

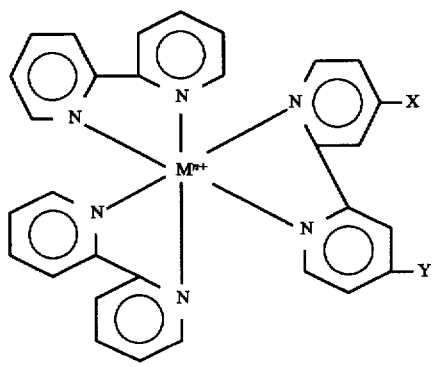

wherein:
n is the integer 1, 2 or 3,
M is ruthenium or osmium,

X is a substituent containing an N-hydroxysuccinimide ester group, or a substituent containing a carboxylate group Y is a substituent containing an N-hydroxysuccinimide ester group, or a substituent containing a carboxylate group, or each of X and Y is —CH$_2$Cl; or a salt of said compound.

11. A compound of the structure:

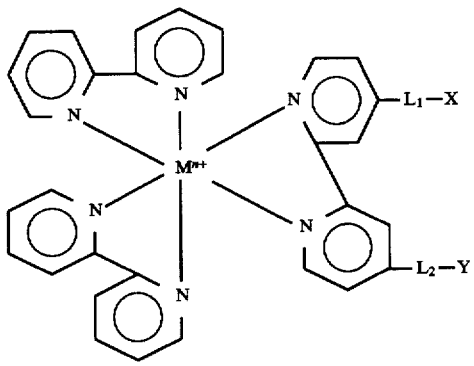

wherein:

n is the integer 1, 2 or 3,

M is ruthenium or osmium,

L$_1$ is a covalent bond or straight or branched alkyl, aryl or aralkyl,

L$_2$ is a covalent bond or straight or branched alkyl, aryl or aralkyl,

X is an N-hydroxysuccinimide ester or carboxylate group; and,

Y is an N-hydrocysuccinimide ester or a carboxylate group, or each of X and Y is —CH$_2$Cl; or a salt of said compound.

12. A compound which is suitable for forming a species capable of being induced to electrochemiluminescence, said compound having the formula

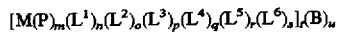

wherein:

M is ruthenium or osmium;

P is a polydentate ligand of M;

L$^1$, L$^2$, L$^3$, L$^4$, L$^5$ and L$^6$ are ligands of M, which are the same or not all the same;

m is an integer equal to or greater than 1;

each of n, o, p, q, r and s is zero or a positive integer;

X is either an N-hydroxysuccinimide ester group or a carboxylate moiety covalently bound to one or more of P, L$^1$, L$^2$, L$^3$, L$^4$, L$^5$, L$^6$ either directly or via a C$_1$–C$_{10}$ branched or unbranched, substituted or unsubstituted alkyl or aralkyl group;

Y is either an N-hydroxysuccinimide ester group or a carboxylate group covalently bound to one or more of P, L$^1$, L$^2$, L$^3$, L$^4$, L$^5$, L$^6$ either directly or via a C$_1$–C$_{10}$ branched or unbranched, substituted or unsubstituted alkyl or aralkyl group;

P, L$^1$, L$^2$, L$^3$, L$^4$, L$^5$, L$^6$ and being of such composition and number that the species formed from said precursor is capable of being induced to electrochemiluminesce, and the total number of bonds to M provided by the ligands of M equals the coordination number of M.

13. A composition which comprises a chemical compound having the formula

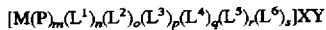

wherein:

M is ruthenium or osmium;

P is a bidentate aromatic heterocyclic nitrogen-containing ligand of M selected from the group consisting of bipyridyl, substituted bipyrdyl, bipyrazyl, substituted bipyrazyl, phenanthrolyl and substituted phenanthrolyl, wherein each of said substituted groups is substituted by an alkyl, aryl, aralkyl, carboxylate, carboxaldehyde, carboxamide, cyano, amino, hydroxycarbonyl, hydroxyamino, aminocarbonyl, amidine, guanidinium, ureide, sulfur-containing group, phosphorus-containing group, and the carboxylate ester of N-hydroxysuccinimide L$^1$ and L$^2$, independently of one another, each is a bidentate aromatic heterocyclic nitrogen-containing ligand of M selected from the group consisting of bipyridyl, substituted bipyridyl, bipyrazyl, substituted bipyrazyl, phenanthrolyl and substituted phenanthrolyl, wherein each of said substituted groups is substituted by an alkyl, aryl, aralkyl, carboxylate, carboxaldehyde, carboxamide, cyano, amino, hydroxycarbonyl, hydroxyamino, aminocarbonyl, amidine, guanidinium, ureide, sulfur-containing group, phosphorus-containing group, or the carboxylate ester of N-hydroxysuccinimide; or is a monodentate ligand including carbon monoxide, cyanides, isocyanides, halides, and aliphatic, aromatic and heterocyclic phosphines, amines, stilbines, and arsines;

L$^3$, L$^4$, L$^5$ and L$^6$ each is a monodentate ligand selected from the group consisting of carbon monoxide, cyanides, isocyanides, halides, and aliphatic, aromatic and heterocyclic phosphines, amines, stilbines, and arsines; and each of P, L$^1$, L$^2$, L$^3$, L$^4$, L$^5$ and L$^6$ being the same or not the same as each other ligand;

B is a substance covalently bound to one or more of P, L$^1$, L$^2$, L$^3$, L$^4$, L$^5$ through one or more linkages;

m is 1;

each of n, o, p, q, r and s is zero or 1;

t is an integer equal to or greater than 1; and u is 1;

such that:

when two of said L ligands are bidentate the compound has the formula

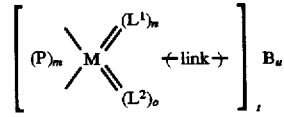

with n and o being 1; p, q, r and s being zero; and said link being covalent bonding, electrostatic bonding, or hydrogen bonding linking B with at least one of P, M, L$^1$ or L$^2$; or when one of said L ligands is bidentate the compound has the formula

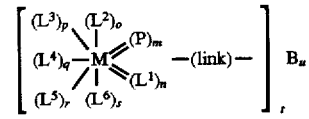

with n, o, p, q, r and s each being zero or 1; and said link being covalent bonding, electrostatic bonding, or hydrogen bonding linking B with at least one of P, M, L$^1$, L$^2$, L$^3$, L$^4$, L$^5$ and L$^6$; or when none of said L ligands is bidentate the compound has the formula

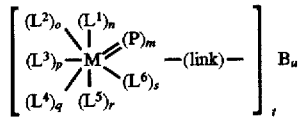

with n, o, p, q, r and s each being zero or 1; and said link being covalent bonding, electrostatic bonding, or hydrogen bonding linking B with at least one of P, M, $L^1$, $L^2$, $L^3$, $L^4$, $L^5$ and $L^6$; and P, $L^1$, $L^2$, $L^3$, $L^4$, $L^5$ and $L^6$ and B being of such composition and number that the chemical compound is capable of being induced to electrochemiluminesce, and the total number of bonds to M provided by the ligands of M equals the coordination number of M.

* * * * *